(12) United States Patent
Schmidt

(10) Patent No.: US 9,434,867 B2
(45) Date of Patent: Sep. 6, 2016

(54) BISPHENOL A (BPA) FREE EPOXY RESINS

(71) Applicant: University of Massachusetts Lowell, Boston, MA (US)

(72) Inventor: Daniel Schmidt, Tewksbury, MA (US)

(73) Assignee: University of Massachusetts Lowell, Boston, MA (US)

( * ) Notice: Subject to any disclaimer, the term of this patent is extended or adjusted under 35 U.S.C. 154(b) by 0 days.

(21) Appl. No.: 14/860,131

(22) Filed: Sep. 21, 2015

(65) Prior Publication Data

US 2016/0075923 A1 Mar. 17, 2016

Related U.S. Application Data

(62) Division of application No. 13/823,477, filed as application No. PCT/US2012/035481 on Apr. 27, 2012, now Pat. No. 9,139,690.

(60) Provisional application No. 61/501,566, filed on Jun. 27, 2011, provisional application No. 61/479,633, filed on Apr. 27, 2011.

(51) Int. Cl.
| | |
|---|---|
| *C09J 163/00* | (2006.01) |
| *C07D 303/28* | (2006.01) |
| *C08G 59/24* | (2006.01) |
| *C08G 65/26* | (2006.01) |
| *C09D 163/00* | (2006.01) |
| *C08K 5/17* | (2006.01) |

(52) U.S. Cl.
CPC ............ *C09J 163/00* (2013.01); *C07D 303/28* (2013.01); *C08G 59/24* (2013.01); *C08G 65/2609* (2013.01); *C09D 163/00* (2013.01); *C08K 5/17* (2013.01)

(58) Field of Classification Search
CPC  C08G 65/2609; C08G 59/24; C09D 163/00; C07D 303/28; C09J 163/00
See application file for complete search history.

(56) References Cited

U.S. PATENT DOCUMENTS

| | | | |
|---|---|---|---|
| 3,297,724 | A | 1/1967 | McConnell et al. |
| 3,410,825 | A | 11/1968 | Coover, Jr. et al. |
| 3,950,451 | A | 4/1976 | Suzuki et al. |
| 6,777,088 | B2 | 8/2004 | Walker et al. |
| 2004/0082805 | A1 | 4/2004 | Eguchi et al. |
| 2004/0225025 | A1 | 11/2004 | Sullivan et al. |
| 2009/0023885 | A1 | 1/2009 | Beall et al. |
| 2013/0143982 | A1 | 6/2013 | Jin et al. |

FOREIGN PATENT DOCUMENTS

| | | |
|---|---|---|
| FR | 1477931 A | 4/1967 |
| JP | 58074714 | 5/1983 |
| WO | 2011/068644 A1 | 6/2011 |
| WO | 2012/044458 A1 | 4/2012 |
| WO | 2012/091701 A1 | 7/2012 |

OTHER PUBLICATIONS

Alcón, José M., et al., "Advanced Flame-Retardant Expoy Resins from Phosphorus-Containing Diol", Journal of Polymer Science; Part A: Polymer Chemistry, 2005, vol. 43, pp. 3510-3515.
Bantle, Siegfried, et al., "Branching in epoxy resins: molecular weight as a function of the extent of reaction and critical behaviour", Polymer, May 1986, vol. 27, pp. 728-734.
Booth, Chad J., et al., "Copolyterephthalates Containing Tetramethylcyclobutane with Impact and Ballistic Properties Greater than bisphenol A polycarbonate", Polymer, 2006 vol. 47, pp. 6398-6405.
Dufton, Peter, "Lightweight Thermoset Composites: Materials in Use, Their Processing and Applications", Rapra Technology Limited, 2000, p. 10.
International Search Report relating to PCT International Application No. PCT/US2012/35481, dated Sep. 28, 2012.
Momentive Product Bulletin; EPON™ and EPI-REZ™ Epoxy Resins, Momentive Speciality Chemicals, Inc., 2011, pp. 1-15.
Montanari, Angela, et al., "Quality of organic coatings for food cans: evaluation techniques and prospects of improvement", Progress in Organic Coatings, 1996, vol. 29, pp. 159-165.
Murguía, Marcelo C., et al., "Selective Preparation of Key Intermediates for the Synthesis of Gemini Surfactants by Phase-Transfer Catalysis", Reaction Kinetics and Catalysis Letters, 2002, vol. 75, No. 2, pp. 205-211.
Nootens, C., et al., "A New Phenolic Resole Curing Agent for High Performance Can Coatings Based on Low VOC Content Lacquers", Surface Coatings International, 1997, pp. 50-56.
Parmar, Randhir, et al., "A comparative study of waterborne epoxy-acrylic graft copolymer dispersion based coatings and solvent based coatings for can coating applications", Paintindia, Mar. 2004, vol. 54, No. 3, pp. 51-52, 54, 56-58, 60, 62-64.
Romano, Robert J. et al., "High Performance Bisphenol A (BPA) Free Epoxy Resins", Toxics Use Reduction Institute Academic Research Program, University of Massachusetts Lowell, Technical Report No. 66, Oct. 2010, pp. 1-14.
Somerville, George R., et al., "Defunctionalizing Technique for Producing Epoxy Resin-Phthalic Alkyds", Industrial and Engineering Chemistry, vol. 49, No. 7, Jul. 1957, pp. 1080-1084.
Subrayan, R.P., et al., "Catalysis of Thermally Curable High Solids Cycloaliphatic Epoxy Formulations", Polymeric Materials: Science & Engineering, 2001, vol. 85, pp. 1 -4.
Watkins, Michael J., "Making Epoxy Resins Using Phosphonium Halide Catalysts", Tech Notes, Cypress Chemical Consulting, Inc., Feb. 2011, pp. 1-4.
Written Opinion of the International Searching Authority relating to PCT International Application No. PCT/US2012/35481, dated Sep. 28, 2012.

*Primary Examiner* — Robert Jones, Jr.
(74) *Attorney, Agent, or Firm* — McCarter & English, LLP; Danielle L. Herritt, Esq.; Patrick A. Walker, III

(57) ABSTRACT

An epoxy resin is provided that includes a diglycidyl ether of a substituted cycloaliphatic diol or bis-thiol, and a thermoset epoxy polymer is provided employing the same. The epoxy resin is bisphenol A free, and capable of forming thermoset epoxy polymers with fewer associated health and environmental concerns than conventional epoxies based on phenolic compounds.

13 Claims, 13 Drawing Sheets

BISPHENOL A (BPA) FREE EPOXY RESINS

RELATED APPLICATIONS

This application is a divisional application of U.S. application Ser. No. 13/823,477, issued as U.S. Pat. No. 9,139,690, filed Mar. 14, 2013 and accorded a filing date of May 24, 2013. U.S. application Ser. No. 13/823,477 is the 35 U.S.C. 371 national stage filing of International Application No. PCT/US2012/035481, filed Apr. 27, 2012. International Application No. PCT/US2012/035481 claims priority to U.S. Provisional Patent Application Nos. 61/479,633, filed Apr. 27, 2011 and No. 61/501,566, filed Jun. 27, 2011. The entire contents of the foregoing applications are hereby incorporated by reference, and priority to each of the foregoing applications is claimed.

FIELD OF THE INVENTION

The present disclosure is directed to an epoxy resin composition based on diglycidyl ether(s) of substituted cycloaliphatic diol(s) and epoxy thermosets prepared using the same. Substituted cycloaliphatic diol diglycidyl ethers are rigid molecules that, upon polymerization, can form a rigid thermoset epoxy having desirable properties. Such properties include sufficient flexibility (e.g., $T_g$ values of about 30° C. to about 100° C.), adhesion, reactivity and high heat resistance for use in a range of applications such as food and beverage containers, or in adhesives. Fewer health and environmental concerns are associated with the resulting thermoset epoxy polymer than conventional resins based on bisphenol A and related phenolic compounds.

The epoxy resin of the present disclosure is made without bisphenols, minimizing the potential of the resulting thermoset epoxy polymer to release estrogenic or endocrine disrupting compounds. The epoxy resin of the present disclosure is an alternative to based epoxy thermosets based on phenolic compounds both in general and in particular for applications where the potential health effects of such compounds (including bisphenol A, BPA, and related bisphenols) are a concern.

BACKGROUND OF THE INVENTION

A need exists for a novel epoxy resin capable of forming BPA free epoxy. The present disclosure provides a new epoxy resin containing diglycidyl ether(s) of substituted cycloaliphatic diol(s) that is capable of forming a rigid thermoset epoxy that is BPA free but exhibits properties similar to BPA based epoxies.

SUMMARY OF THE INVENTION

It is an object of the present disclosure to provide an epoxy resin capable of forming a thermoset wherein the thermoset is BPA free. It is another object of the present disclosure to provide an epoxy resin capable of forming a rigid thermoset epoxy polymer suitable for various applications, such as in a food or beverage container or as an adhesive.

The present disclosure is directed to an epoxy resin composition comprising a first monomer represented by formula (I):

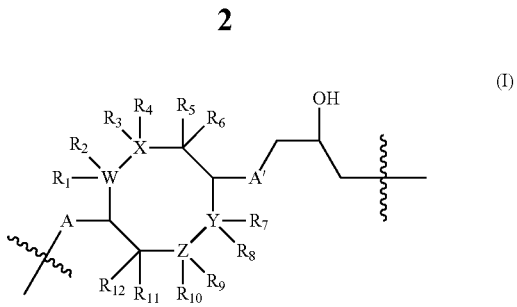

wherein A and A' are each independently selected from the group consisting of O and S; wherein W, X, Y and Z are each independently selected from the group consisting of a bond, C, N, O, Si or S; wherein $R_1$-$R_{12}$ are each independently selected from hydrogen, a $C_1$-$C_6$ alkyl group, a $C_2$-$C_6$ alkenyl group, a $C_5$-$C_7$ membered aromatic ring, or a $C_3$-$C_8$ cycloalkyl or heterocycle; wherein adjacent R groups may optionally form a fused ring selected from a $C_5$-$C_7$ membered aromatic ring, or a $C_3$-$C_8$ cycloalkyl or heterocycle; wherein the alkyl, alkenyl, ring or fused ring is optionally substituted with one or more substituents, each of which is independently selected from $NH_2$, OH, $CF_3$, CN, $CO_2H$, C(O) or halogen; provided that at least one R group selected from $R_1$-$R_{12}$ is not hydrogen; and/or one or more additional monomers and/or a curative compounds. The additional monomer(s) may also be independently represented by formula (I) as well as other formulas contained herein. The present disclosure is also directed to a thermoset epoxy polymer comprising the epoxy resin and one or more curative compounds.

The present disclosure is also directed to a container comprising a food-contact surface, wherein at least a portion of the food-contact surface is coated with a composition comprising the epoxy resin as described herein.

The present disclosure is also directed to a method of preparing a container comprising a substrate having a food-contact surface, the method comprising providing a coating composition comprising an epoxy resin as described herein, applying the coating composition to at least a portion of the food-contact surface of the substrate, and forming a container from the substrate, wherein the applying step may be performed prior to or after the forming step.

The present disclosure is also directed to a method of preparing a high molecular weight epoxy resin using a two step synthesis wherein the same catalyst is used in both steps. In the first step, the diglycidyl ether of the diol may be synthesized under alkaline conditions via the reaction of the diol with excess epichlorohydrin in the presence of a phase transfer catalyst. In the second step, a high molecular weight chain-extended epoxy may be synthesized via the reaction of the diglycidyl ether with additional diol in the presence of a phase transfer catalyst. The same phase transfer catalyst may be used for both steps, reducing purification requirements between the two steps.

The present disclosure is also directed to an adhesive comprising the epoxy resin as described herein.

Finally, the present disclosure is directed to a thermoset epoxy polymer comprising an epoxy resin as described herein and a curative compound.

DETAILED DESCRIPTION OF THE INVENTION

Figure 1:
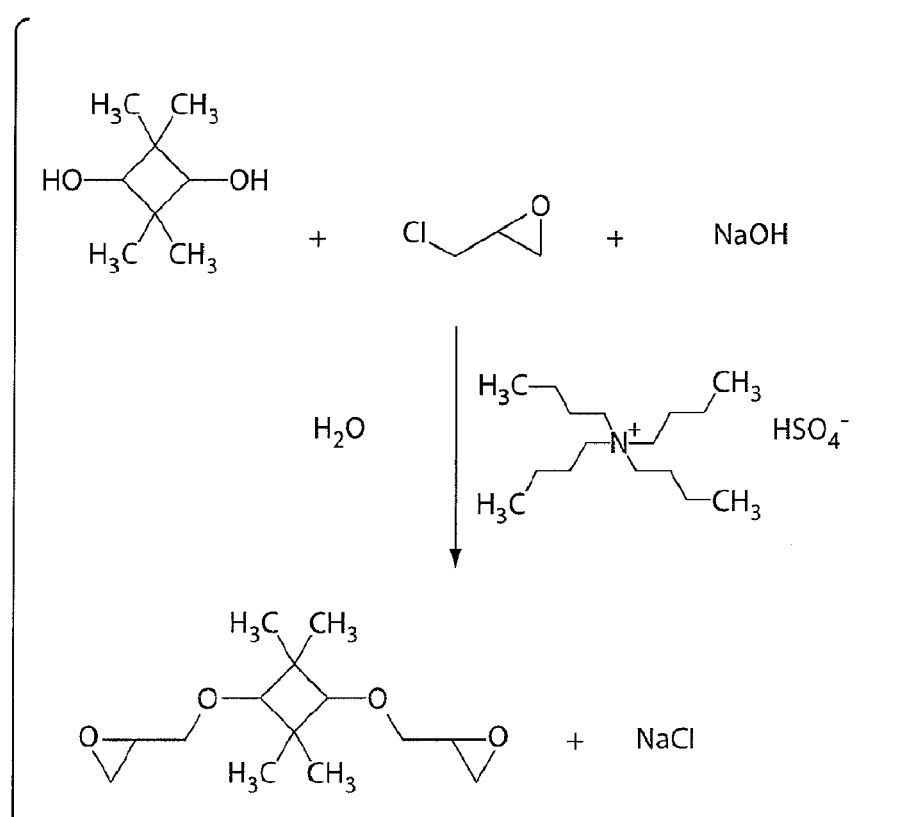
FIG. 1 shows the synthesis of 2,2,4,4-tetramethyl-1,3-cyclobutanediol diglycidyl ether (CBDO-DGE) from the reaction of 2,2,4,4-tetramethyl-1,3-cyclobutanediol (CBDO), epichlorohydrin and sodium hydroxide in the presence of a phase transfer catalyst, tetra-n-butylammonium bromide (TBAB).

The present disclosure provides an epoxy resin based on diglycidyl ether(s) of substituted cycloaliphatic diol(s) and polymers prepared using the same. In some embodiments, the epoxy resin forms a rigid thermoset epoxy polymer with stability, mechanical and thermomechanical properties similar to or better than conventional epoxies, such as epoxy resins based on bisphenol A diglycidyl ether (BADGE), at a similar cost but without the health concerns associated with the use of bisphenol A (BPA).

BPA polycarbonate has the following structure:

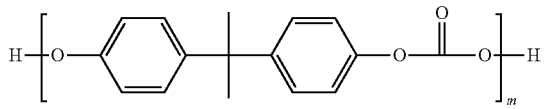

BPA-based epoxy resins, including BADGE-based resins, include free BPA either via unreacted BPA or via resin degredation. The presence of BPA is significant because these resins are used in food packaging and BPA has been linked to serious health and environmental concerns. This concern is due, in part, to BPA's structural similarity to estrogen. BPA has been implicated as an endocrine disruptor with various potential adverse health effects.

In one embodiment, the present disclosure is directed to an epoxy resin composition including (a) a first monomer represented by formula (I):

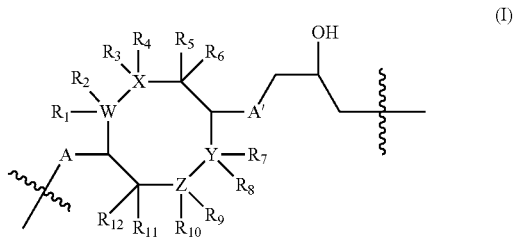

wherein A and A' are each independently selected from the group consisting of O and S; wherein W, X, Y and Z are each independently selected from the group consisting of a bond, C, N, O, Si or S; wherein $R_1$-$R_{12}$ are each independently selected from hydrogen, a $C_1$-$C_6$ alkyl, a $C_2$-$C_6$ alkenyl group, a $C_5$-$C_7$ membered aromatic ring, or a $C_3$-$C_8$ cycloalkyl or heterocycle; wherein adjacent R groups may optionally form a fused ring selected from a $C_5$-$C_7$ membered aromatic ring, or a $C_3$-$C_8$ cycloalkyl or heterocycle; wherein the alkyl, alkenyl, ring or fused ring is optionally substituted with one or more substituents, each of which is independently selected from $NH_2$, OH, $CF_3$, CN, $CO_2H$, C(O) or halogen; provided that at least one R group selected from $R_1$-$R_{12}$ is not hydrogen; and (b) one or more additional monomers.

The one or more additional monomers may be selected from the group consisting of an aliphatic, cycloaliphatic or polyetheric molecule comprising at least two functional groups, e.g. hydroxyl or epoxy groups. They may impart flexibility and/or toughness to the epoxy resin. Polyetheric molecules include any poly ether based molecule, such as polypropylene oxide (PPO), e.g. short PPO chains with epoxy end groups. Examples of additional monomers include linear $C_2$-$C_{12}$ aliphatic diol compounds; unsubstituted or dimethanol substituted $C_4$-$C_8$ cycloaliphatic rings; and polyetheric molecules based on polymers or copolymers of ethylene oxide, propylene oxide, tetrahydrofuran or glycidyl ethers of any of the above-mentioned compounds. The one or more additional monomer may also be independently represented by formula (I).

In one embodiment, the present disclosure is directed to an epoxy resin composition including (a) a first monomer represented by formula (I):

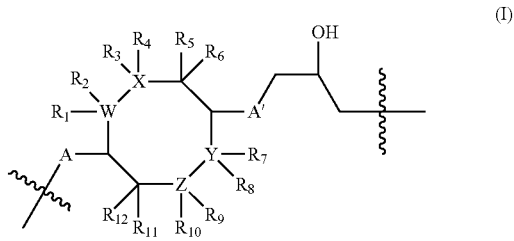

wherein A and A' are each independently selected from the group consisting of O and S; wherein W, X, Y and Z are each independently selected from the group consisting of a bond, C, N, O, Si or S; wherein $R_1$-$R_{12}$ are each independently selected from hydrogen, a $C_1$-$C_6$ alkyl, a $C_2$-$C_6$ alkenyl group, a $C_5$-$C_7$ membered aromatic ring, or a $C_3$-$C_8$ cycloalkyl or heterocycle; wherein adjacent R groups may optionally form a fused ring selected from a $C_5$-$C_7$ membered aromatic ring, or a $C_3$-$C_8$ cycloalkyl or heterocycle; wherein the alkyl, alkenyl, ring or fused ring is optionally substituted with one or more substituents, each of which is independently selected from $NH_2$, OH, $CF_3$, CN, $CO_2H$, C(O) or halogen; provided that at least one R group selected from $R_1$-$R_{12}$ is not hydrogen; and (b) a curative compound.

In another embodiment, the present disclosure is directed to an epoxy resin composition wherein the first monomer is represented by formula (II):

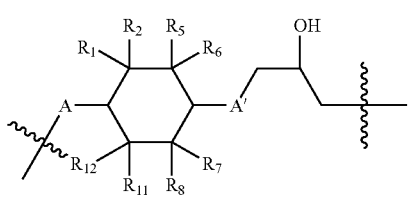

(II)

wherein A, A', $R_1$, $R_2$, $R_5$, $R_6$, $R_7$, $R_8$, $R_{11}$ and $R_{12}$ are defined above.

In another embodiment, the present disclosure is directed to an epoxy resin composition wherein the first monomer is represented by formula (III):

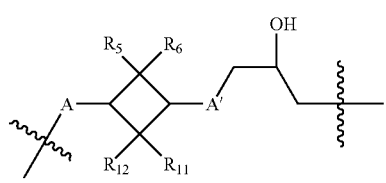

(III)

wherein A, A', $R_5$, $R_6$, $R_{11}$ and $R_{12}$ are defined above.

The present disclosure is also directed to an epoxy resin composition wherein A and A' are both either O or S; wherein W, X, Y and Z are independently selected from the group consisting of a bond and C; wherein $R_1$-$R_{12}$ are independently selected from hydrogen, $C_1$-$C_6$ straight chain or branched alkyl or alkenyl group; and wherein the alkyl, alkenyl is optionally substituted with one or more substituents, each of which is independently selected from $NH_2$, OH, $CF_3$, CN, $CO_2H$, C(O) or halogen.

The present disclosure is also directed to an epoxy resin composition wherein A and A' are both O; wherein W, X, Y and Z are independently selected from the group consisting of a bond and C; wherein $R_1$-$R_{12}$ are independently selected from hydrogen, $C_1$-$C_6$ straight chain or branched alkyl.

Finally, the present disclosure is also directed to an epoxy resin composition wherein $R_1$-$R_{12}$ are independently selected from methyl or ethyl groups.

In some embodiments, examples of the first monomer include diglycidyl ethers of the following diols:

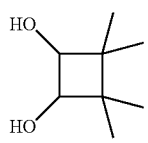
3,3,4,4-tetramethyl-1,2-cyclobutanediol

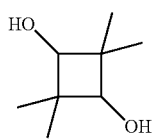
2,2,4,4-tetramethyl-1,3-cyclobutanediol

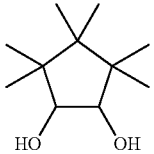
3,3,4,4,5,5-hexamethyl-1,2-cyclopentanediol

-continued

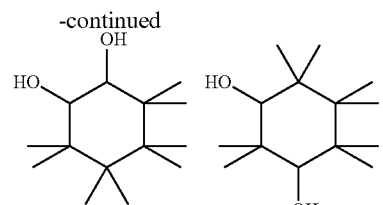

2,2,4,4,5,5-hexamethyl-1,3-cyclopentanediol 3,3,4,4,5,5,6,6-octamethyl-1,2-cyclohexanediol 2,2,4,4,5,5,6,6-octamethyl-1,3-cyclohexanediol

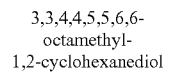 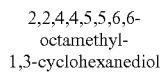

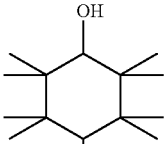  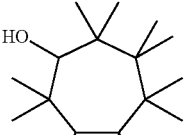

2,2,3,3,5,5,6,6-octamethyl-1,4-cyclohexanediol 3,3,4,4,5,5,6,6,7,7-decamethyl-1,2-cycloheptanediol 2,2,4,4,5,5,6,6,7,7-decamethyl-1,3-cycloheptanediol

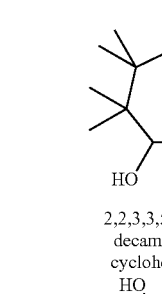 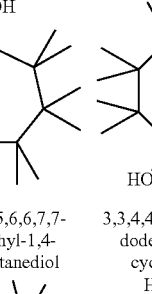

2,2,3,3,5,5,6,6,7,7-decamethyl-1,4-cycloheptanediol 3,3,4,4,5,5,6,6,7,7,8,8,-dodecamethyl-1,2-cyclooctanediol

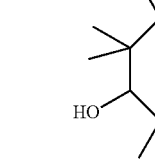 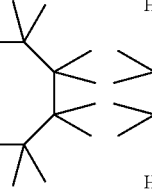

2,2,4,4,5,5,6,6,7,7,8,8-dodecamethyl-1,3-cyclooctanediol 2,2,3,3,5,5,6,6,7,7,8,8-dodecamethyl-1,4-cyclooctanediol

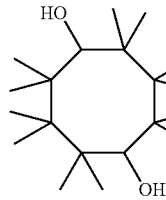 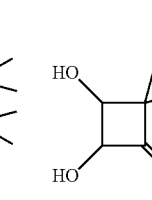

2,2,3,3,4,4,6,6,7,7,8,8-dodecamethyl-1,5-cyclooctanediol 4,4-dimethyl-1-cyclobutanone-2,3-diol 1,2,-cyclobutanedione-3,4-diol

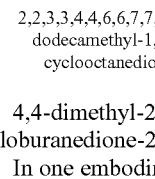

4,4-dimethyl-2-cyclobutanone-1,3-diol and 1,3-cycloburanedione-2,4-diol.

In one embodiment, the first monomer is diglycidyl ether of 2,2,4,4-tetramethyl-1,3-cyclobutanediol. In other embodiment, the first monomer is diglycidyl ether of cyclohexanedimethanol (DGE-CHDM). In yet another embodiment, the first monomer is diglycidyl ether of 2,2,4,4-tetramethyl-1,3-cyclobutanediol and the additional monomer is diglycidyl ether of cyclohexanedimethanol (DGE-CHDM).

The diols disclosed herein may also be substituted for equivalent compounds wherein one or more of the OH groups are replaced with SH groups (i.e. bis-thiols), the C(O) groups are replaced with C(S) groups, or mixtures thereof.

The monomers include saturated and unsaturated cycloaliphatic compounds. The diols may have isomerism, e.g. a cis and a trans isomer. Different isomers may have different properties, such as reactivity or sensitivities under reaction conditions. In one embodiment, one isomer may be present in a greater amount relative to the other isomer. In some embodiments, the diol of the present disclosure may be present as a pure isomer, e.g. cis or trans, or may be any mixture of both isomers.

In some embodiments, the present disclosure is directed to an epoxy resin composition, comprising:
(a) a monomer of formula (III)

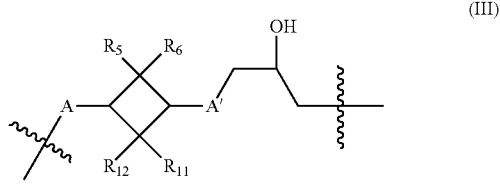

(III)

wherein A and A' are each independently O or S; wherein $R^5$, $R^6$, $R^{11}$ and $R^{12}$ are each independently alkyl; and
(b) a hardener, such as a polyamine or a polythiol hardener.

The monomer, or monomers, and the curative compound may have a stoichiometric ratio of epoxy (or epoxide) groups to amine reactive groups of about 0.8:1.2 to about 1.2:0.8, preferably about 0.9:1.1 to about 1.1:0.9, and more preferably about 1:1. In some embodiments, the curative compound is a polyamine hardener. Preferably, the stoichiometric ratio epoxy groups in the monomer(s) to amine hydrogens of the hardener is about 0.8:1.2 to about 1.2:0.8, preferably about 0.9:1.1 to about 1.1:0.9, and more preferably about 1:1.

As provided above, the present disclosure teaches epoxy resin composition comprising fused rings. Exemplary monomers that comprise diglycidyl ethers of diols comprising fused rings include as norborane, norbornene, bicycle[2.2.2]octane, decalin, cubane, adamantine camphor and derivatives thereof. Such derivatives include camphordiol, camphanediol and norcamphanediol.

The term "alkyl" includes fully saturated branched or unbranched (or straight chair or linear) hydrocarbon moieties, comprising from 1 to 20 carbon atoms. In some embodiments, the alkyl comprises 1 to 6 carbon atoms or 1 to 4 carbon atoms. Representative examples of alkyl include methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl and n-heptyl. The term "$C_1$-$C_6$ alkyl" includes a hydrocarbon having one to six carbon atoms.

The term "alkenyl" includes branched or unbranched hydrocarbon moieties having at least one carbon-carbon double bond. The term "$C_2$-$C_6$ alkenyl" includes hydrocarbons having two to six carbon atoms and comprising at least one carbon-carbon double bond. Representative examples of alkynyl moieties include ethenyl, prop-1-enyl, butenyl, isopropenyl or isobutenyl.

The term "cycloalkyl" includes saturated or partially unsaturated but non-aromatic monocyclic or bicyclic hydrocarbon groups of 3-8 carbon atoms. In some embodiments, the cycloalkyl groups have 3-6 carbon atoms. For bicyclic and tricyclic cycloalkyl systems, all rings are non-aromatic. Representative examples of monocyclic cycloalkyl groups include cyclopropyl, cyclobutyl, cyclopentyl, cyclopentenyl, cyclohexyl, cyclohexenyl, cycloheptyl and cyclooctyl. Representative bicyclic cycloalkyl groups include bornyl, decahydronaphthyl, bicyclo[2.1.1]hexyl, bicyclo[2.1.1]heptyl, bicycle[2.2.1]heptenyl and bicyclo[2.2.2]octyl. The term "($C_3$-$C_8$) cycloalkyl" includes cyclic hydrocarbon groups having 3 to 8 carbon atoms.

The term "aromatic ring" includes monocyclic or bicyclic aromatic hydrocarbon groups having 5-7 carbon atoms in the ring portion, as well as aromatic heterocycles. Representative examples of aromatic rings are phenyl, naphthyl, hexahydroindyl, indanyl, tetrahydronaphthyl and furan. The term "$C_5$-$C_7$ aromatic rings" includes aromatic hydrocarbon rings having 5 to 7 carbon atoms in the ring portion.

As used herein, the term "heterocyclic ring" includes saturated or unsaturated non-aromatic rings (partially unsaturated) or ring systems, e.g., which is a 3-, 4-, 5-, 6-, 7-, 8-, 9- or 10-membered monocyclic, 5-, 6-, 7-, 8-, 9-, 10-, 11-, or 12-membered bicyclic or 10-, 11-, 12-, 13-, 14- or 15-membered tricyclic ring system and contains at least one heteroatom selected from O, S and N, in which the N and S may be oxidized to various oxidation states. The term "$C_3$-$C_8$-heterocycle" includes saturated or unsaturated non-aromatic rings (partially unsaturated) or ring systems comprising 3 to 8 carbon atoms and containing at least one heteroatom selected from O, S and N, in which the N and S may be oxidized to various oxidation states. For bicyclic and tricyclic heterocyclyl ring system, a non-aromatic ring system is defined as being a non-fully or partially unsaturated ring system. Therefore bicyclic and tricyclic heterocyclyl ring systems includes heterocyclyl ring systems in which one of the fused rings is aromatic but the other(s) is (are) non-aromatic. In some embodiment, heterocyclyl moiety represents a saturated monocyclic ring containing from 3-10 ring atoms and optionally containing a further heteroatom, selected from O, S or N. The heterocyclic group can be attached at a heteroatom or a carbon atom. The heterocyclyl can include fused or bridged rings as well as spirocyclic rings. Examples of heterocycles include dihydrofuranyl, dioxolanyl, dioxanyl, dithianyl, piperazinyl, pyrrolidinyl, dihydropyranyl, oxathiolanyl, dithiolanyl, oxathianyl, thiomorpholino, oxiranyl, aziridinyl, oxetanyl, oxepanyl, azetidinyl, tetrahydrofuranyl, tetrahydrothiophenyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl.

The present disclosure teaches an epoxy resin composition comprising diglycidyl ether(s) of diol(s) comprising fused rings, provided the fused ring is not isosorbide, isomannide and isoidide.

In some embodiments, the epoxy resin exhibits sufficient flexibility/rigidity for use in a range of applications such as food and beverage containers. One source of rigidity comes from the substitution on the cycloaliphatic portion of the epoxy resin. Sufficient rigidity may be obtained by a single substitution on the cycloaliphatic ring provided the substituent is sufficiently bulky to sterically hinder the ring. In one embodiment, the cycloaliphatic ring is substituted with one substituent. In another embodiment, the cycloaliphatic ring is substituted with at least two substituents. The present disclosure is also directed to an epoxy resin wherein at least two R groups are not hydrogen.

In some embodiments, the epoxy resin of the present disclosure possesses high flexibility in addition to the ability to form a coating with high performance properties (e.g. rigidity, adhesion, and chemical resistance). A sufficiently flexible epoxy resin imparts flexibility to a cured coating composition. The flexibility imparted to a cured coating composition overcomes rigidity problems associated with prior epoxy-based compositions. A flexible epoxy resin also has a lower the glass transition temperature ($T_g$) as an uncured coating composition, which improves flow of the coating composition during cure and lowers the viscosity of the coating composition.

In some embodiments, the epoxy resin of the present disclosure has a $T_g$ of about 30° C. to about 100° C. Within this range, the epoxy resin is sufficiently flexible to permit deformation of a cured coating composition without forming cracks, and is sufficiently hard to exhibit excellent chemical and mar resistance. Preferably, the epoxy resin of the present disclosure has a $T_g$ of about 45° C. to about 80° C.

The epoxy resin of the present disclosure may also have a $T_g$ value equivalent to, or less than, traditional bisphenol A based epoxy resins. By varying the composition of the epoxy resin and/or the preparation conditions, various $T_g$ values can be achieved. In some embodiments, the epoxy resin of the present disclosure can have a $T_g$ value of less than about 100° C., 90° C., 80° C., 70° C., 60° C., 50° C., 40° C., 30° C. or 20° C., while still exhibiting suitable chemical and mar resistance properties.

Flexibility of an epoxy resin coating may also be determined by the Impact Wedge Bend test of ASTM D3281-84. This test specifies an impact process to produce a cone-shaped bend 100 mm long. The epoxy resin coating of the present disclosure may have a Wedge Bend value equivalent to, or greater than, traditional bisphenol A based epoxy resins. By varying the composition of the coating and/or the preparation conditions, various Wedge Bend values can be achieved. The length of the crack along the bend after processing may also be measured and recorded as the crack length. Coating flexibility is inversely related to the crack length. In some embodiments, the crack length is less than about 100 mm, 90 mm, 80 mm, 70 mm, 60, mm, 50 mm, 40 mm, 30 mm, 20 mm, or 10 mm Adhesion of an epoxy resin coating may be determined by standard adhesion ASTM test methods, e.g. ASTM D1002-10, ASTM D1876 (T-Peel), ASTM D3359 or ASTM D3164. The epoxy resin coating of the present disclosure may have an adhesion value equivalent to, or greater than, traditional bisphenol A based epoxy resins. By varying the composition of the coating and/or the preparation conditions, various adhesion values can be achieved. In some embodiments, the epoxy resin coating of the present disclosure may have a Stress at Break value of greater than about 2 MPa, 3 MPa, 4 MPa, 5 MPa, 6 MPa, 7 MPa, 8 MPa, 9 MPa, 10 MPa, or about 11 MPa per ASTM D1002-10. The epoxy resin coating of the present disclosure may also have a Load at Machine Break value of greater than about 1000 N, 2000 N, 2500 N, 3000 N, 3500 N, 4000 N or about 4500 N per ASTM D1002.10. In other embodiments, the epoxy resin coating of the present disclosure can have a D3359 adhesion value of greater than 0A, 0B, 1A, 1B, 2A, 2B, 3A, 3B, 4A or 4B.

Sensitivity of an epoxy resin coating to solvent attack may be determined by the MEK rub solvent resistance test of ASTM D5402 using methyl ethyl ketone. The epoxy resin coating of the present disclosure may have a MEK rub solvent resistance test value equivalent to, or greater than, traditional bisphenol A based epoxy resins. By varying the composition of the coating and/or the preparation conditions, various MEK rub solvent resistance test values can be achieved. In some embodiments, the epoxy resin coating of the present disclosure can have a MEK rub solvent resistance test value of greater than about 50, 55, 60, 65, 70, 75, 80, 85, 90, 95 or 100 (double rubs).

In some embodiments, the epoxy resin coating of the present disclosure can withstand elevated temperature conditions frequently associated with retort processes or other food or beverage preservation or sterilization processes. The epoxy resin coating of the present disclosure may have a heat resist properties equivalent to, or better than, traditional bisphenol A based epoxy resins. In some embodiments, the epoxy resin coating of the present disclosure can withstand exposure, for a suitable time period (e.g., for between at least about 10 seconds and about 90 minutes), to temperatures of at least about 80° C., more preferably at least about 100° C., and even more preferably at least about 120° C., while still exhibiting suitable film or coating properties (as defined, for example, by the aforementioned tests).

In some embodiments, the epoxy resin coating of the present disclosure can withstand being exposed to conditions that include one of the above temperatures in combination with pressures of at least about 0.5 atm above atmospheric pressure and more preferably at least about 1.0 atm above atmospheric pressure, while still exhibiting suitable film or coating properties (as defined, for example, by the aforementioned tests).

The epoxy resin composition of the present disclosure comprises a ratio of first monomer to second monomer ranging from about 0.1:99.9 to about 99.9:0.01. Preferably, the epoxy resin composition comprises a ratio of first monomer to second monomer of about 20:80 to about 99.9:0.01. More preferably, the epoxy resin composition comprises at least 20% by weight of the first monomer, based on the total weight of the epoxy resin.

The epoxy resin composition of the present disclosure is BPA free and capable of providing a sufficiently rigid thermoset epoxy polymer for a variety of applications, e.g., adhesives, food and beverage containers, including coatings for food and beverage containers. The presence of BPA in resins used for food packaging is significant because BPA is linked to serious health and environmental concerns. In one embodiment, the epoxy resin composition of the present disclosure is substantially free of phenolic hydroxyls. In another embodiment, the thermoset epoxy polymer of the present disclosure is substantially free of bisphenols.

The term "substantially free" means that the compositions of the present disclosure contain less than 100 parts per million (ppm) of the recited compound.

The present disclosure is also directed to a thermoset epoxy polymer comprising an epoxy resin composition comprising a monomer represented by formula (I) and one or more curative compounds. In one embodiment, the thermoset epoxy polymer comprises a first monomer represented by formula (I), a second monomer and a curative compound. The curative (i.e., epoxy crosslinker/curative) compound may be selected from known crosslinker or curative compounds that cure or crosslink epoxy resins. Examples of curative compounds include formaldehyde hardeners and polyamine hardeners. Formaldehyde hardeners include phenol-formaldehyde, resorcinol-formaldehyde, catechol-formaldehyde, hydroquinone-formaldehyde, cresol-formaldehyde, phloroglucinol-formaldehyde, pyrogallol-formaldehyde, melamine-formaldehyde, urea-formaldehyde, and blends or derivatives thereof. Polyamine hardeners include aliphatic or alicyclic polyamines, such as ethylenediamine (EDA), diethylenetriamine (DETA), triethylenetetramine (TETA), tetraethylenepentamine (TEPA), polyoxypropylenediamine, polyoxypropylenetriamine, isophorone diamine, menthane diamine, bis(4-amino-3-methyldicyclohexyl)methane and the like.

The epoxy resin of the present disclosure preferably has a weight average molecule weight ($M_w$) of less than about 100,000 Daltons, more preferably less than about 75,000 Daltons, and most preferably less than about 50,000 Daltons. $M_w$ is determined using standard analytical techniques, such as gel permeation chromatography against polystyrene standards.

In one embodiment, the epoxy resin exhibits a viscosity similar to currently available materials used in can coating applications. In can coatings, material such as EPON™ 1007 and EPON™ 1009 are often used. These materials consist of BPA-based epoxies that are solid at room temperature and are supplied in solution form. EPON™ materials typically exhibit a viscosity of less than about 200 poise at 25° C. measured as a 75% weight solution of resin solids in xylene.

The epoxy resin of the present disclosure preferably has a viscosity of less than about 1000 poise at 25° C. measured as a 40% weight solution of resin solids in methyl ethyl ketone or equivalent solvent. More preferably, the epoxy resin has a viscosity of less than about 750 poise at 25° C. measured as a 40% weight solution of resin solids in methyl ethyl ketone or equivalent solvent. Most preferably, the epoxy resin has a viscosity of less than about 500 poise at 25° C. measured as a 40% weight solution of resin solids in methyl ethyl ketone or equivalent solvent.

In some embodiments, the epoxy resin, e.g. CBDO-DGE, has a significantly lower viscosity than epoxies based on phenolic compounds, e.g. BADGE. Not wishing to be bound by any particular theory, it is believed that the reduced viscosity is because the molecular weight of the epoxy resin of the present disclosure is proportionately less than, e.g. about half, of the equivalent phenolic material as a result of its compact structure and lack of aromatic rings. The advantage of this reduced viscosity is the epoxy resin of the present disclosure can form a more intimate coating on an object as compared to the equivalent phenolic material. For example, the less viscous epoxy resin of the present disclosure may be applied to a surface and penetrate more spaces and cover more surface area than the equivalent phenolic material.

Figure 13:
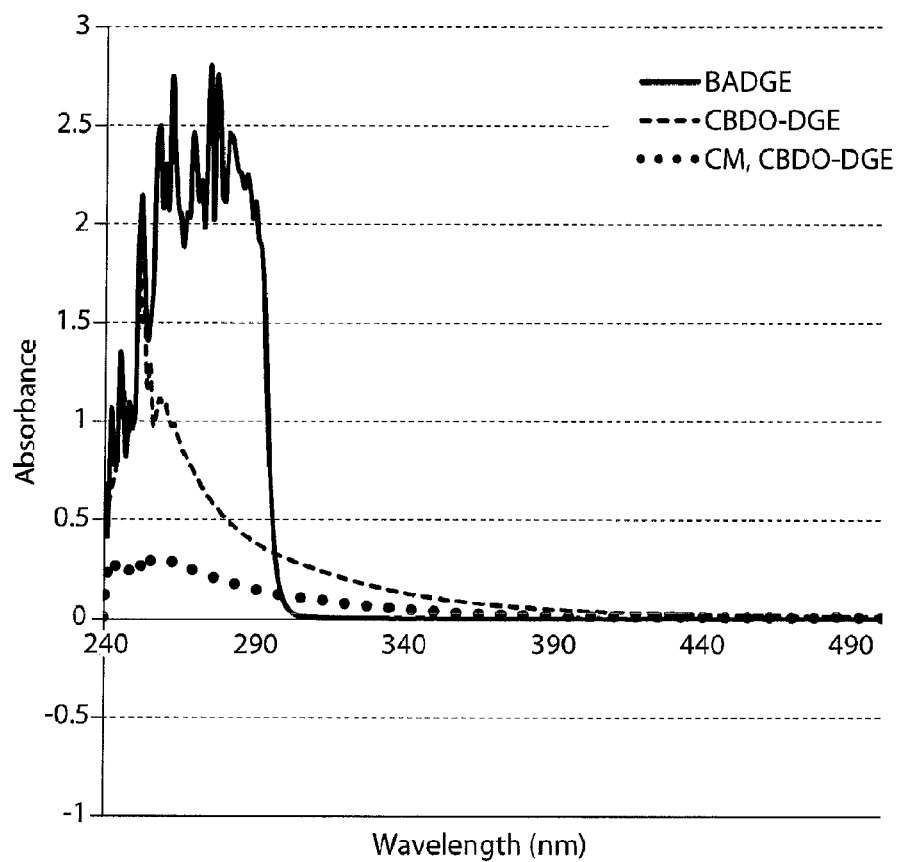
FIG. 13 shows a comparison of the UV absorbance of CBDO-DGE; commercial CBDO-DGE and BADGE.

The epoxy resin, and the thermoset epoxy polymer comprising the epoxy resin, of the present disclosure naturally exhibit limited UV absorbance, especially as compared to phenolic based epoxies. See FIG. 13. The limited UV absorbance is due to, in part, the absence of phenolic groups. Phenolic based epoxies can be engineered to have limited UV absorbance, but only if chemically modified in some fashion. Such additional modification is costly, time consuming and potentially negatively affect the performance of the epoxy resin and thermoset epoxy polymer. For example, hydrogenated BPA are known for applications that require UV resistance. To achieve hydrogenated BPA, however, the material must undergo the extra reaction step (hydrogenation) which potentially degrades its (thermo)mechanical properties. The limited UV absorption of the materials of the present disclosure also allows for epoxy crosslinking via a photoinitiator. Photoinitiation is less effective where thick layers of epoxy resin are present and the epoxy resin exhibits UV absorbance itself.

Synthesis

The synthesis of diglycidyl ethers of substituted cycloaliphatic diols may be performed by any known route, preferably using the reaction of the substituted cycloaliphatic diol directly with epichlorohydrin. See U.S. Pat. Nos. 7,619,056; 3,041,300 and 3,225,067, the entirety of which are incorporated by reference herein.

Epoxy resins may be hardened or cured by any known route. The chemistry of epoxy curing is explained in great detail in the *Handbook of Composites*, edited by S T Peters, Chapter 3, pp 48-74, published by Chapman & Hall, 1998, ISBN 0 412 54020 7.

An epoxy resin comprising a diglycidyl ether of a diol can be synthesized using a two step process, in particular, a two step process using two different phase transfer catalysts. For example, in the first step, the diglycidyl ether of the diol may be synthesized under alkaline conditions via the reaction of the diol with excess epichlorohydrin in the presence of tetrabutylammonium bisulfate plus aqueous sodium hydroxide. In the second step, a high molecular weight chain-extended epoxy may be synthesized via the reaction of the diglycidyl ether with additional diol, same or different, in the presence of a ethyltriphenylphosphonium iodide under water-free conditions. In the second step, a "cationic curing", homopolymerizatoin catalyst or acid catalyst may be used as the phase transfer catalyst. These catalysts may be selected from perchloric, trifluoromethanesulfonic, perfluororalkyl-sulfonic, tetrafluoroboric and hexafluorophosphoric acids, boron trifluoride, heteropoly acids (e.g. 12-tungustophosphric acid and 9-molybudo-3-vanadophosphoric acid) and quaternary ammonium hexafluoroantimonate salt.

Using a different catalyst for each step, however, requires the purification of the diglycidyl ether of the diol after preparation, potential adjustments to pH and aqueous/anhydrous environments. This may be performed by removing the excess epichlorohydrin (volatile) and excess NaOH (solid, filtered out). Removal of the phase transfer catalyst used in the first step is not trivial and may involve additional processing steps. Contamination of the initial phase transfer catalyst may interfere with the second step. The present disclosure relates to the selection of a catalyst that catalyzes both reaction steps and/or is soluble to be effective in both steps.

In one embodiment, the present disclosure is directed to a method of preparing a high molecular weight epoxy resin using a two step synthesis wherein the same catalyst is used in both steps. For example, an epoxy resin comprising a diglycidyl ether(s) of cycloaliphatic diol(s) may be prepared by a method using a common or single catalyst. In the first step, the diglycidyl ether of the diol may be synthesized under alkaline conditions via the reaction of the diol with excess epichlorohydrin in the presence of a first phase transfer catalyst. In the second step, a high molecular weight chain-extended epoxy may be synthesized via the reaction of the diglycidyl ether with additional diol, same or different, in the presence of a second phase transfer catalyst. The first and second phase transfer catalysts may be the same, reducing purification requirements between the two steps.

The present disclosure also relates to a method of preparing a chain extended epoxy resin comprising reacting a first cycloaliphatic molecule with epichlorohydrin in the presence of a catalyst under alkaline conditions to form a diglycidyl ether, and then reacting the diglycidyl ether with a second cycloaliphatic molecule in the presence of the catalyst to form the chain extended epoxy resin. The first and second cycloaliphatic molecules may both be diols or they may both be bis-thiols. They may also be both the same diol or the same bis-thiol.

In one embodiment, the first and second cycloaliphatic molecules are both independently selected from the group consisting of 3,3,4,4-tetramethyl-1,2-cyclobutanediol; 2,2,4, 4-tetramethyl-1,3-cyclobutanediol; 3,3,4,4,5,5-hexamethyl-1,2-cyclopentanediol; 2,2,4,4,5,5-hexamethyl-1,3-cyclopentanediol; 3,3,4,4,5,5,6,6-octamethyl-1,2-cyclohexanediol; 2,2,4,4,5,5,6,6-octamethyl-1,3-cyclohexanediol; 2,2,3,3,5,5,6,6-octamethyl-1,4-cyclohexanediol; 3,3,4,4,5,5,6,6,7,7-decamethyl-1,2-cycloheptanediol; 2,2,4,4,5,5,6,6,7,7-decamethyl-1,3-cycloheptanediol; 2,2,3,3,5,5,6,6,7,7-decamethyl-1,4-cycloheptanediol; 3,3,4,4,5,5,6,6,7,7,8,8-dodecamethyl-1,2-cyclooctanediol; 2,2,4,4,5,5,6,6,7,7,8,8-dodecamethyl-1,3-cyclooctanediol; 2,2,3,3,5,5,6,6,7,7,8,8-dodecamethyl-1,4-cyclooctanediol; 2,2,3,3,4,4,6,6,7,7,8,8-dodecamethyl-1,5-cyclooctanediol; 4,4-dimethyl-1-cyclobutanone-2,3-diol; 1,2-cyclobutanedione-3,4-diol; 4,4-dimethyl-2-cyclobutanone-1,3-diol; 1,3-cycloburanedione-2,4-diol; and diol derivatives of norbornane, norbornene, bicycle[2.2.2]octane, cubane and adamantine.

The phase transfer catalyst may be selected from tetrabutylammonium salts, such as bisulfate and hydroxide, as well as benzyl triethyl ammonium salts. Chloride salts may also be used. In some embodiments, quaternary phosphonium salts, such as ethyltriphenylphosphonium iodide, may be selected as the phase transfer catalyst. These catalysts may be water-sensitive.

The amount of phase transfer catalyst used is preferably an amount sufficient to catalyze the formation of diglycidyl ether as well as the high molecular weight chain-extended epoxy. The amount of catalyst may range from about 0.01 to about 50 mol %, preferably about 0.02 to about 20 mol %. In one embodiment, about 1.0 to about 20 mol % is used in the first step. In another embodiment, about 10 mol % catalyst is used in the first step. To be clear, 10 mol % means 0.1 moles phase transfer catalyst for every 1 mole of diol. In some embodiments, only a small amount of catalyst is required. These embodiments may include the use of quaternary phosphonium catalysts or quaternary ammonium salts. For example, about 0.1 to about 1.0 mol % of these catalysts may be used in the second step.

Applications

The epoxy resin, and thermoset epoxy polymer, of the present disclosure may be used to coat the surfaces of packaging articles (e.g., food and beverage cans). In one embodiment, the present disclosure provides a container comprising a food-contact surface, wherein at least a portion of the food-contact surface is coated with a composition comprising an epoxy resin as described herein.

In another embodiment, the present disclosure provides a method of preparing a container comprising a substrate having a food-contact surface, the method comprising providing a coating composition comprising an epoxy resin of formula (I), applying the coating composition to at least a portion of the food-contact surface of the substrate; and forming a container from the substrate, wherein the applying step may be performed prior to or after the forming step.

In one embodiment, the container is a food or beverage can and the surface of the container is the surface of a metal substrate. The material can be applied to a metal substrate either before or after the substrate is formed into a food or beverage can (e.g., two-piece cans, three-piece cans) or portions thereof, whether it be a can end or can body. The material can be used in injection molding applications, e.g., drinking bottles, drinking glasses, or in sheet/film applications.

A coating composition of the present disclosure may also include other optional ingredients that do not adversely affect the coating composition or a cured coating composition resulting therefrom. Such optional ingredients are typically included in a coating composition to enhance composition aesthetics, to facilitate manufacturing, processing, handling, and application of the composition, and to further improve a particular functional property of a coating composition or a cured coating composition resulting therefrom. For example, a composition that includes a polymer of the present disclosure may optionally include crosslinkers, fillers, catalysts, lubricants, pigments, surfactants, dyes, toners, coalescents, extenders, anticorrosion agents, flow control agents, thixotropic agents, dispersing agents, antioxidants, adhesion promoters, light stabilizers, and mixtures thereof, as required to provide the desired film properties. Each optional ingredient is included in a sufficient amount to serve its intended purpose, but not in such an amount to adversely affect a coating composition or a cured coating composition resulting therefrom.

As described above, the materials of the present disclosure may be useful on food and beverage cans (e.g., two-piece cans, three-piece cans, etc.). Two-piece cans are manufactured by joining a can body (typically a drawn metal body) with a can end (typically a drawn metal end). The coatings of the present disclosure are suitable for use in food or beverage contact situations and may be used on the inside of such cans. They may be suitable for spray coating, coil coating, wash coating, sheet coating, and side seam coatings (e.g., food can side seam coatings).

Spray coating includes the introduction of the coated composition into the inside of a preformed packaging container. Typical preformed packaging containers suitable for spray coating include food cans, beer and beverage containers, and the like. The spray preferably utilizes a spray nozzle capable of uniformly coating the inside of the preformed packaging container. The sprayed preformed container is then subjected to heat to remove any residual carriers (e.g., water or solvents) and harden the coating.

A coil coating is described as the coating of a continuous coil composed of a metal (e.g., steel or aluminum). Once coated, the coating coil is subjected to a short thermal, ultraviolet, and/or electromagnetic curing cycle, for hardening (e.g., drying and curing) of the coating. Coil coatings provide coated metal (e.g., steel and/or aluminum) substrates that can be fabricated into formed articles, such as 2-piece drawn food cans, 3-piece food cans, food can ends, drawn and ironed cans, beverage can ends, and the like.

A wash coating is commercially described as the coating of the exterior of two-piece drawn and ironed ("D&I") cans with a thin layer of protectant coating. The exterior of these D&I cans are "wash-coated" by passing pre-formed two-piece D&I cans under a curtain of a coating composition. The cans are inverted, that is, the open end of the can is in the "down" position when passing through the curtain. This curtain of coating composition takes on a "waterfall-like" appearance. Once these cans pass under this curtain of coating composition, the liquid coating material effectively coats the exterior of each can. Excess coating is removed through the use of an "air knife." Once the desired amount of coating is applied to the exterior of each can, each can is passed through a thermal, ultraviolet, and/or electromagnetic curing oven to harden (e.g., dry and cure) the coating.

A sheet coating is described as the coating of separate pieces of a variety of materials (e.g., steel or aluminum) that have been pre-cut into square or rectangular "sheets." Typical dimensions of these sheets are approximately one square meter. Once coated, each sheet is cured. Once hardened (e.g., dried and cured), the sheets of the coated substrate are collected and prepared for subsequent fabrication. Sheet coatings provide coated metal (e.g., steel or aluminum) substrate that can be successfully fabricated into formed articles, such as 2-piece drawn food cans, 3-piece food cans, food can ends, drawn and ironed cans, beverage can ends, and the like.

A side seam coating is described as the spray application of a liquid coating over the welded area of formed three-piece food cans. When three-piece food cans are being prepared, a rectangular piece of coated substrate is formed into a cylinder. The formation of the cylinder is rendered permanent due to the welding of each side of the rectangle via thermal welding. Once welded, each can typically requires a layer of coating, which protects the exposed "weld" from subsequent corrosion or other effects to the contained foodstuff. The coatings that function in this role are termed "side seam stripes." Typical side seam stripes are spray applied and cured quickly via residual heat from the welding operation in addition to a small thermal, ultraviolet, and/or electromagnetic oven.

Other commercial coating application and curing methods are also envisioned, for example, electrocoating, extrusion coating, laminating, powder coating, and the like.

The epoxy resin, and thermoset epoxy polymer, of the present disclosure may be used as an adhesive. For example, the epoxy groups of the diglycidyl ether may react with amine hydrogens of a polyamine hardener. The epoxy resin would be of low to moderate molecular weight, such as less than about 2,000 g/mol, preferably less than 1,000 g/mol. In some embodiments, the molecular weight is low enough to ensure that the epoxy resin is a liquid at or around room temperature. In one embodiment, the epoxy resin is a chain-extended/moderate-MW epoxy in an amine-cured adhesive formulation.

In other embodiments, a two-part epoxy may be used wherein one component is the diglycidyl ether, or a low to moderate MW chain-extended version, and the other component is an amine hardener. Preferably, the viscosities of the two components would be similar, and they would be stored in sealed bottles or syringes under conditions designed to keep them free of any significant contamination. The two components would be applied to the substrate(s) to be bound. The application may be done manually. The components may be applied using a static mixing nozzle and a two-barrel syringe, similar to other commercial systems

EXAMPLES

The present disclosure is described in more detail by the following examples. The present disclosure is, however, not limited by the examples.

Example 1

Synthesis of diglycidyl ether of 2,2,4,4-tetramethyl-1,3-cyclobutanediol (CBDO-DGE) monomer

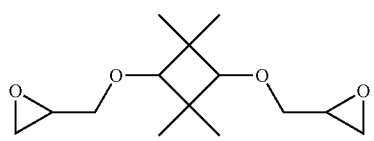 [SMILES: CC1(C)C(OCC2CO2)C(C)(C)C1OCC1CO1]

Figure 2:
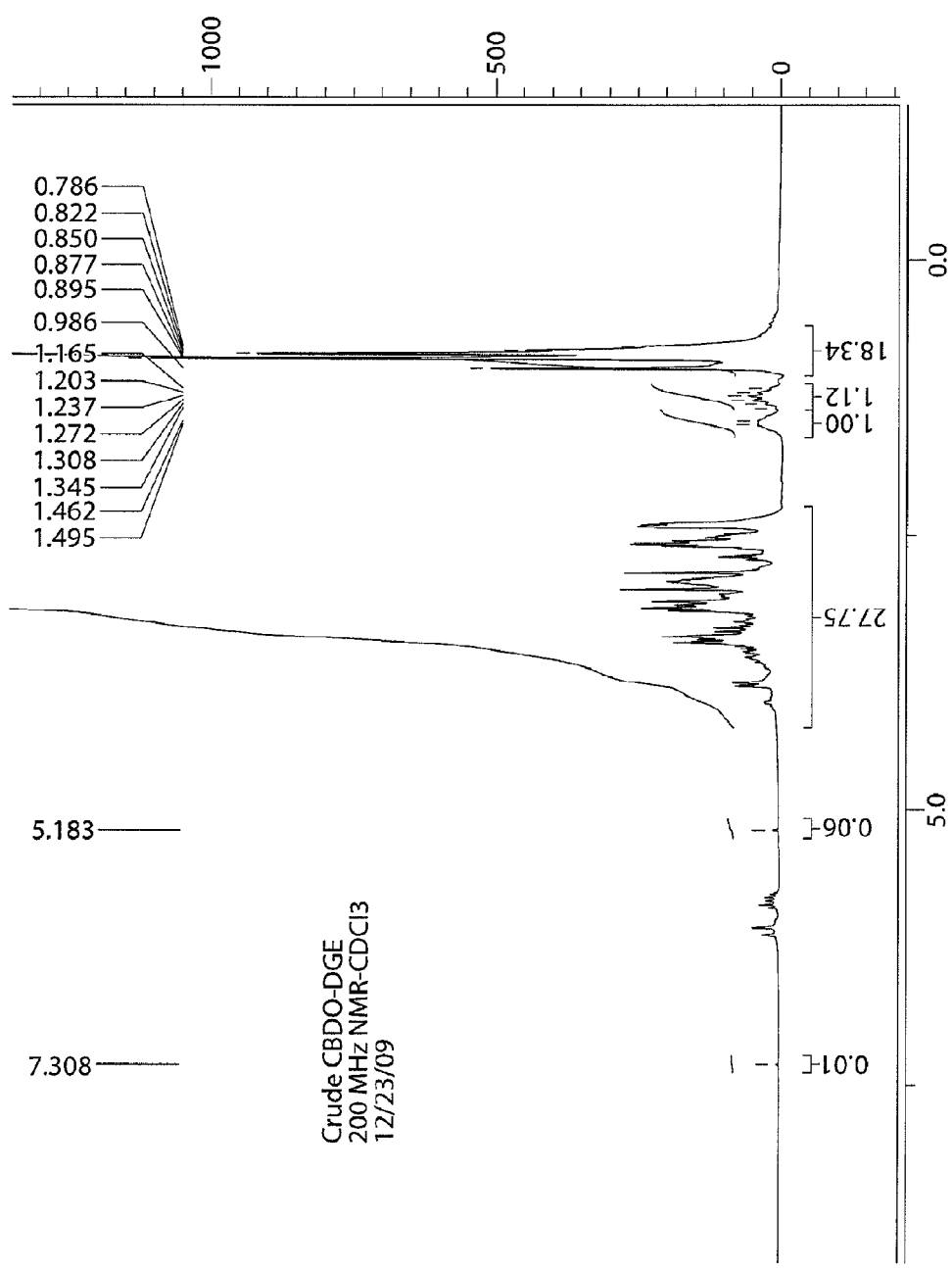
FIG. 2 shows the $^1$H-NMR spectrum of the crude (unpurified) CBDO-DGE product.
Figure 3:
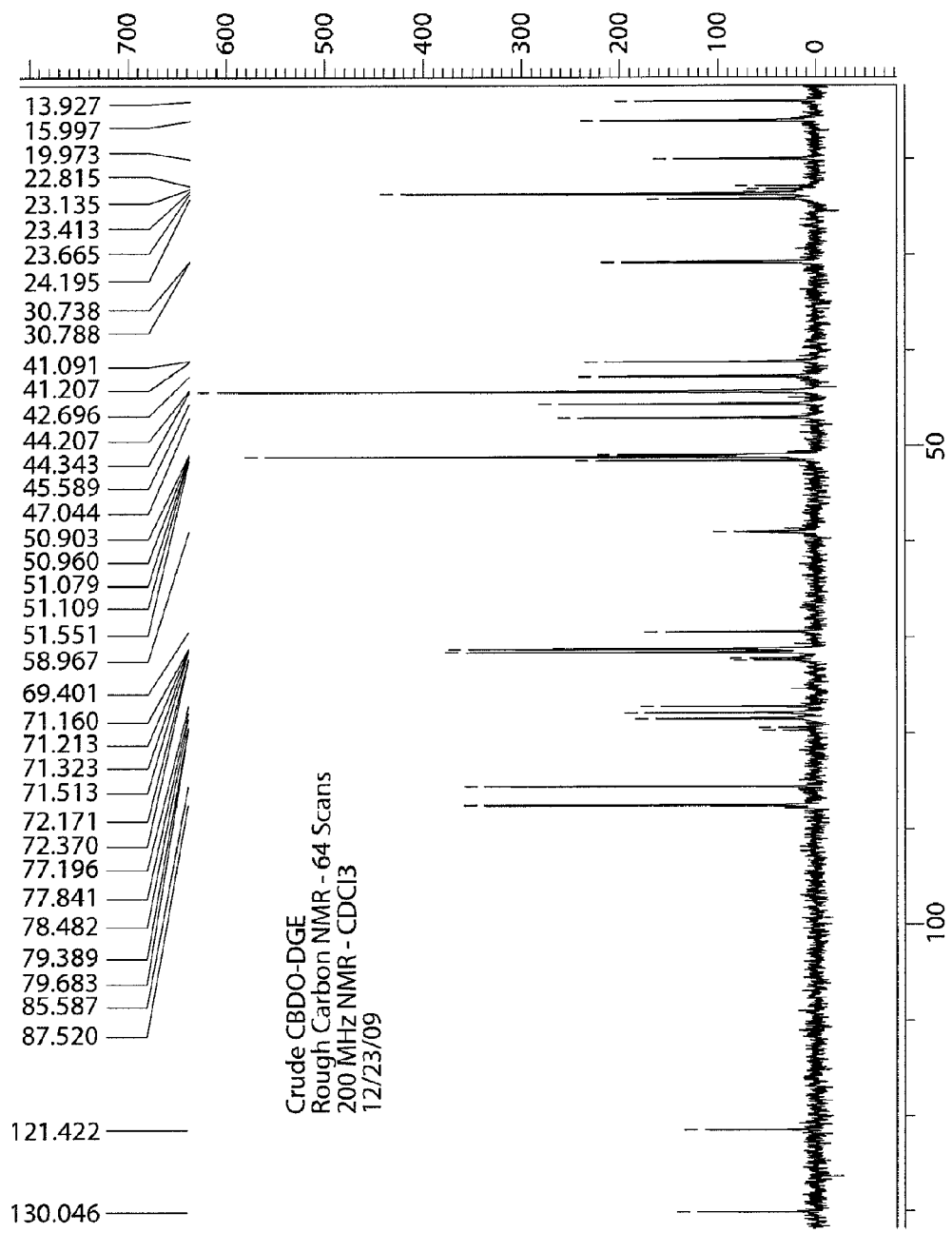
FIG. 3 shows the $^{13}$C-NMR spectrum of the crude CBDO-DGE product.

Initial Synthetic Method: In order to synthesize approximately 10 g of CBDO-DGE, 5.6 g (0.039 mol) of 2,2,4,4-tetramethyl-1,3-cyclobutanediol (CBDO, solid) from TCI America with a cis/trans ratio of 35/65, 31 mL (0.39 mol) of epichlorohydrin (ECH, liquid), 15 g (0.39 mol) of sodium hydroxide (NaOH, solid), and 1.3 g (0.0039 mol) of tetrabutylammonium hydrogen bisulfate (TBAB, solid) phase transfer catalyst were combined in a 250 mL glass reaction bottle, after which 160 µL (0.0087 mol) of deionized water was added and the mixture vigorously stirred with a Teflon®-coated magnetic stir bar while the glass reaction flask was immersed in a silicone oil bath at 40° C. FIG. 1 shows a representative synthesis of the CBDO-DGE monomer. During the reaction, the solution changed from colorless to yellow to orange (the color of the product was dependent on the time allowed for the reaction to occur and varied from batch to batch even under similar reaction conditions). After maintaining the reaction for approximately two hours, the resulting orange product was then diluted with a small amount of dichloromethane to allow for complete transfer to a vacuum filtration setup, where the liquid was separated from the remaining solid sodium hydroxide. The filtered product was then transferred to a 125 mL polypropylene jar, which was left open under a fume hood for approximately twelve hours to allow for the evaporation of the dichloromethane and the excess epichlorohydrin. Finally, the material was placed under vacuum at room temperature for seven days in order to further ensure complete removal of any volatiles (dichloromethane as well as residual water and epichlorohydrin). This yielded a crude product consisting primarily of a mixture of CBDO-DGE and TBAB, as confirmed via $^1$H-NMR and $^{13}$C-NMR spectroscopy (FIGS. 2 and 3).

Figure 4:
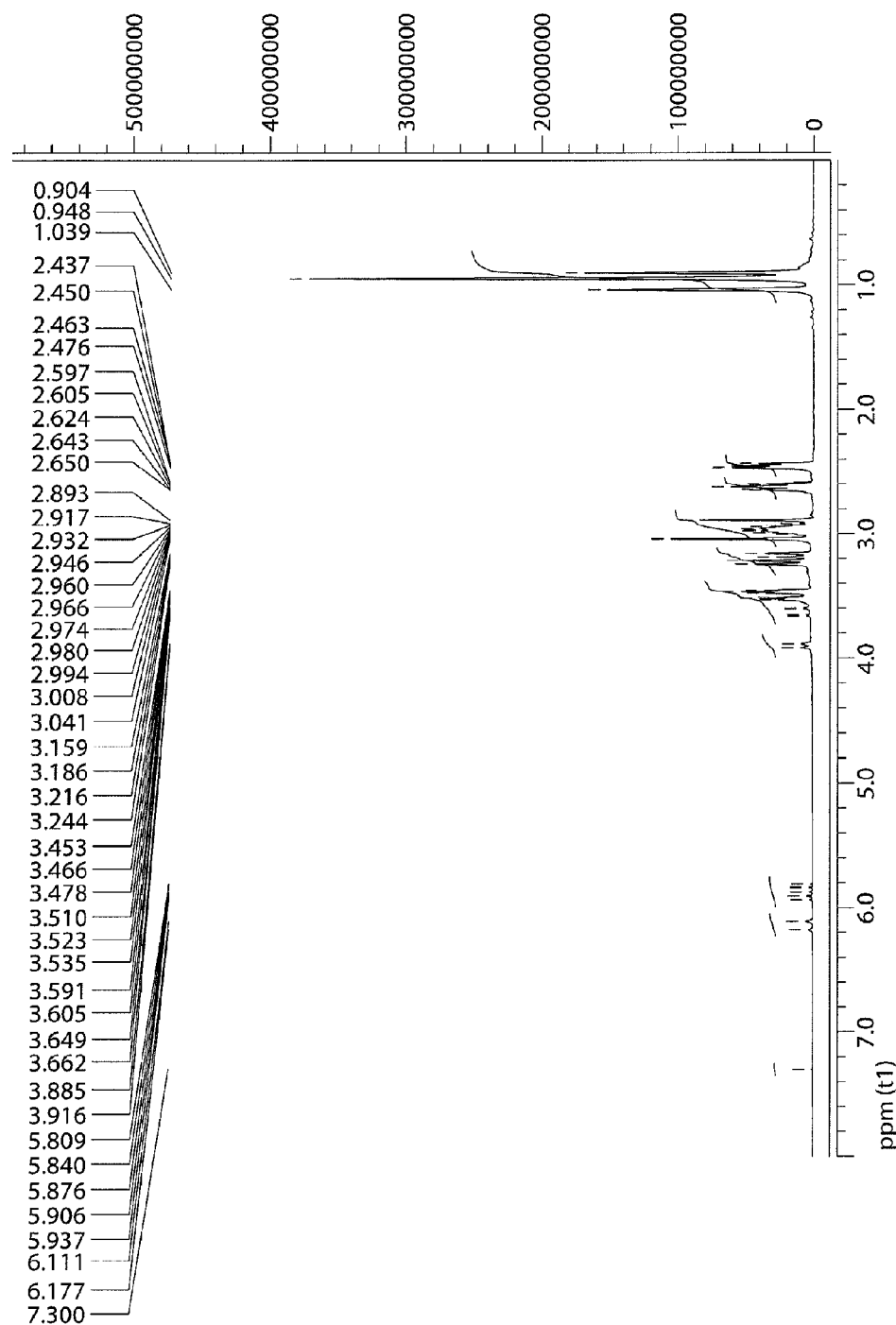
FIG. 4 shows the $^1$H-NMR spectrum of the purified CBDO-DGE product.

TBAB is believed to act as a phase transfer catalyst, shuttling hydroxide anions between the water phase and the organic phase in order to deprotonate the OH groups of the CBDO monomer. This process may create a site where the epoxy groups provided by the epichlorohydrin can attach to the CBDO monomer and form CBDO-DGE. The phase transfer catalyst TBAB was found to be highly soluble in water, and was, therefore, removed from the product through the addition of 75 mL of distilled water to approximately 10 g of product, followed by vigorous stirring for 20 minutes, after which the aqueous layer was decanted, replaced with 75 mL of fresh distilled water, and the process repeated three more times. Once the wash process was completed, the product was placed under vacuum at room temperature for four days in order to remove any residual water from the purified product. The final yield for this method was in the range of 70-80%. The product remained orange in color, indicating the presence of at least trace levels of impurities (pure CBDO-DGE should be colorless). This material is referred to as water-washed CBDO-DGE. The final yield was 7.3701 g (0.029 mol, ~74%) of CBDO-DGE, as confirmed via $^1$H-NMR spectroscopy (FIG. 4). As shown in FIG. 4, $^1$H-NMR spectrum of water-washed CBDO-DGE displays the absence of peaks corresponding to TBAB. This indicated its successful removal, though it should be noted that the orange color of the product remained in spite of the washing.

An alternate process involving an acid wash was also developed to remove impurities from the crude CBDO-DGE. Distilled water with a pH of approximately 4.5-5 in the amount of 75 mL was added to CBDO-DGE. The resulting solution had a pH of 10. Therefore, it was presumed that there was residual NAOH present form the synthesis. Five drops of 60.05 g/mol acetic acid was added to bring the pH to approximately 4. This resulted in a slight color change from a darker brownish orange to a lighter brownish orange. The solution was stirred for 15 minutes using a two inch Teflon®-coated magnetic stir bar. The water was decanted and a fresh 75 mL portion of distilled water was added resulting in a solution with a pH of 4. The solution was stirred again for 15 minutes and the water was then decanted. Once the water was removed, the solution was put in the vacuum oven at 40° C. for 48 hours. This material is referred to as acid-washed CBDO-DGE, as confirmed via $^1$H-NMR spectroscopy. The addition of acetic acid to the washing solution was found to be an effective means of removing both TBAB and residual NaOH as well. The removal of the TBAB and NaOH gives rise to substantial improvements in the mechanical properties, thermal stability and glass transition temperature of the networks.

A Bruker Avance Spectrospin 200 MHz nuclear magnetic resonance (NMR) spectrometer was used to determine the structure and composition of the synthesized products. For example, a CBDO-DGE product (1.0 mL) was diluted with deuterated chloroform (CDCl$_3$) in an NMR tube (5 mm×7" Pyrex tubes rated for 500 MHz NMRs). Water used in each of the washing steps was rotary-evaporated as well, and approximately 0.5-1 mL of the resultant material was diluted with deuterated water (D$_2$O) and analyzed in each case. Proton ($^1$H) and carbon-13 ($^{13}$C) NMR, spectra were obtained using the Xwin software package.

Figure 5:
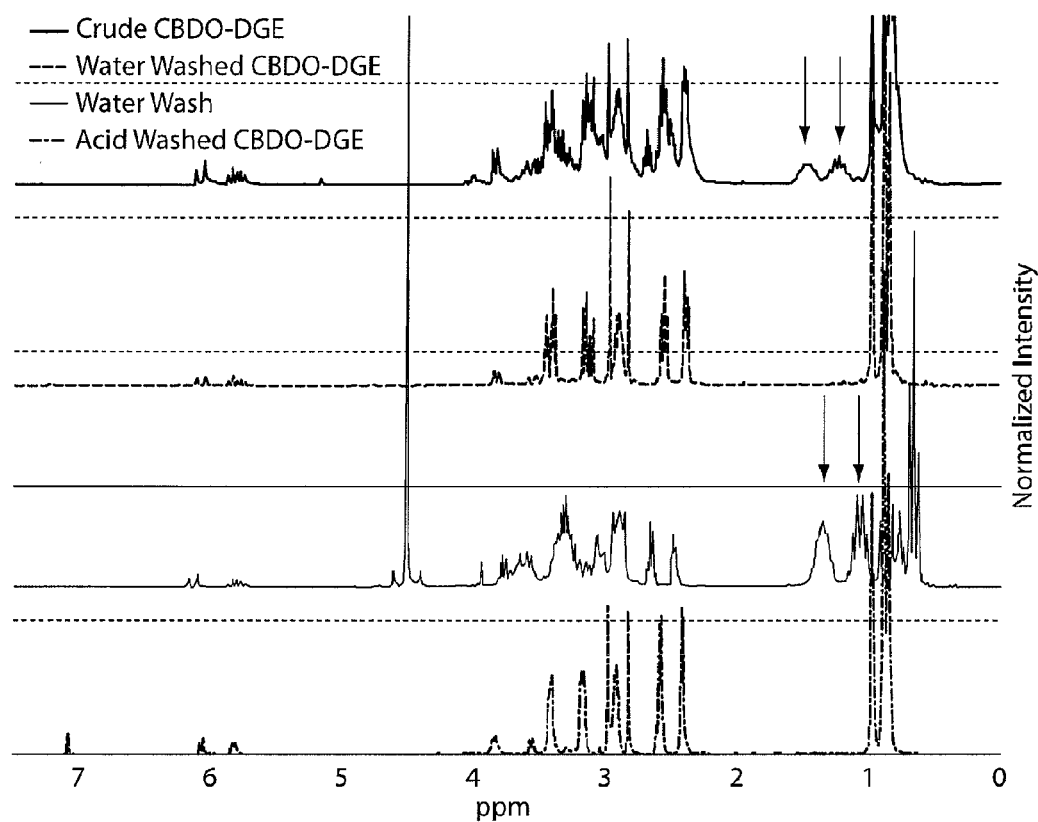
FIG. 5 shows a representative $^1$H-NMR spectrum of crude CBDO-DGE, water wash purified CBDO-DGE, the water wash material, and the acid wash purified CBDO-DGE; arrows indicate peaks assigned to the methylene protons in the TBAB phase transfer catalyst.

A comparison of the $^1$H-NMR spectrum for the crude CBDO-DGE, water washed CBDO-DGE, water wash and acid washed CBDO-DGE is shown in FIG. 5. For the crude CBDO-DGE the peaks at approximately 1.1 and 1.3 ppm, respectively, correspond to the protons of the methylene units of the tetrabutylammonium hydrogen sulfate (TBAB) phase transfer catalyst, indicating that some amount of this material remained in the product. The $^1$H-NMR spectrum of the water used in the initial washing step was also taken. The water wash shows peaks corresponding to TBAB clearly visible at 1.1 and 1.3 ppm in addition to weaker peaks corresponding to some amount of the CBDO-DGE product and/or unreacted CBDO. Once TBAB was confirmed to be soluble in water, a water-based washing procedure was applied and $^1$H-NMR was used to assess the purity of the product at each washing step.

Scale up Synthetic Method: In order to obtain a larger amount (approximately 250 g) of the synthesized CBDO-DGE product, the synthesis described above was scaled up. CBDO monomer from Eastman Chemical Company with a cis/trans ratio of 46/54 was used. This commercially synthesized CBDO-DGE product also contained residual TBAB, and is referred to as crude commercial CBDO-DGE.

The product had a pH of approximately 5 so it was assumed that additional acidification of the product was not necessary. Distilled water with a pH of approximately 4-5 in the amount of 500 mL was added to approximately 50 g of product. The solution was stirred for 15 minutes using a two inch Teflon®-coated magnetic stir bar. The solution turned milky white in appearance and did not separate into two phases until it was allowed to sit overnight. The majority of the aqueous phase was decanted off and a two inch Teflon®-coated magnetic stir was placed inside the flask with the remaining organic phase. The solution was then placed on a hotplate and brought to 100° C. to facilitate the removal of residual water. Ultra high purity nitrogen was used as a carrier gas in order to help remove the steam from the flask. The temperature was held at 100° C. until all the water was evaporated (approximately 15 minutes). During the course of this process the color of the product changed to the yellow-orange color typical for CBDO-DGE synthesized as described previously. Once all water was removed a sharp increase in temperature was observed, with the temperature of the product reaching approximately 120° C. before it was removed from the hot plate. The yield of this purification step was in the range of 60-65%. This material is referred to as water washed commercial CBDO-DGE.

Figure 6:
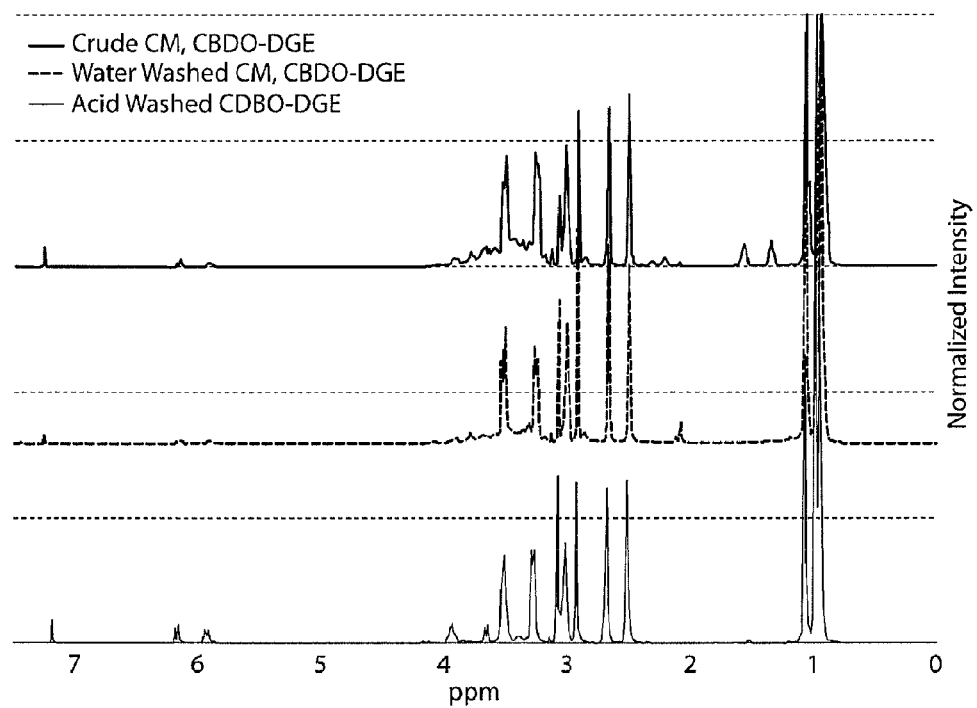
FIG. 6 shows a representative $^1$H-NMR spectrum of crude commercial (CM) CBDO-DGE contaminated with TBAB, the water purified commercial CBDO-DGE and the comparison with acid purified CBDO-DGE.

The NMR spectrum of the commercial CBDO-DGE indicated that there was TBAB present in this material just as in the case of the crude CBDO-DGE (see FIG. 6). The pH of the product was approximately 5 so the water wash method was used rather than the acid wash method. FIG. 6 shows that the TBAB was removed and a purified product was obtained because it lacked the TBAB peaks like the acid purified CBDO-DGE. The acid purified CBDO-DGE spectrum was chosen as a comparison to the purified commercially made CBDO-DGE because the acid purified product provides the most clearly shows the peaks for the CBDO-DGE monomer.

Example 2

Synthesis of High Molecular Weight Epoxy Resin

Figure 7:
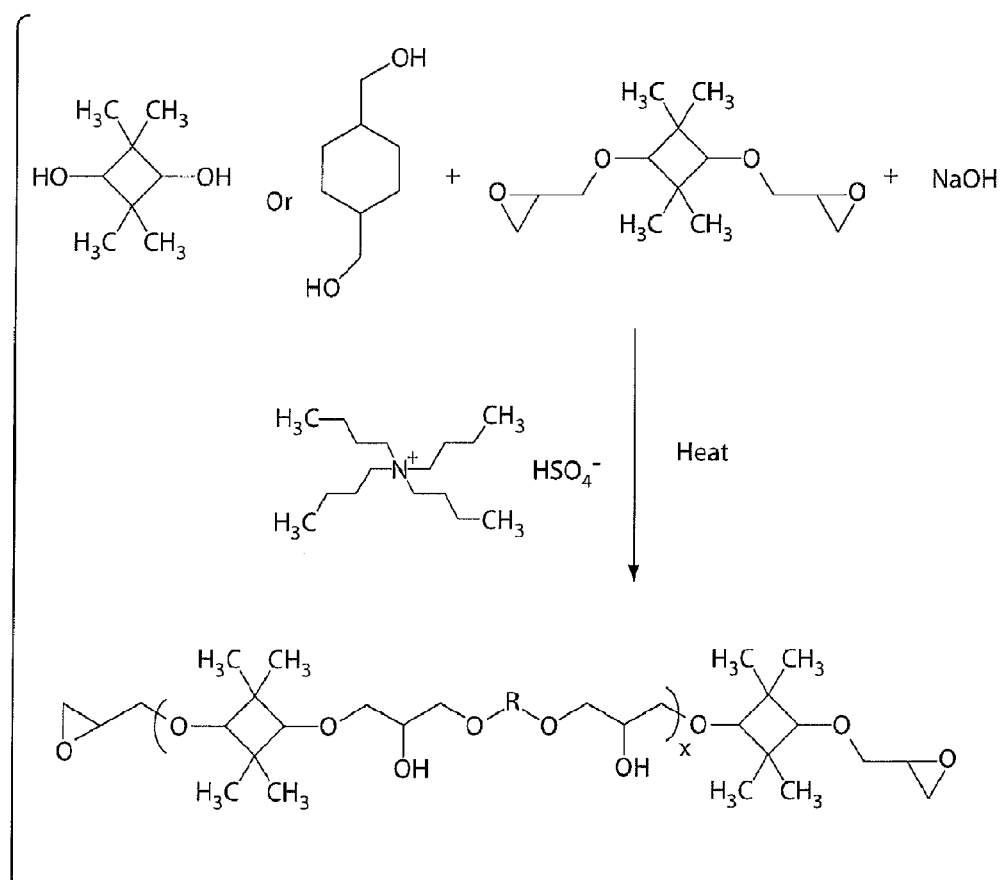
FIG. 7 shows a synthesis of a high molecular weight CBDO-DGE based epoxy resin from the reaction of CBDO or cyclohexanedimethanol (CHDM) with CBDO-DGE in the presence of sodium hydroxide and a phase transfer catalyst (TBAB). In this embodiment, R is derived from CBDO in the case of the CBDO/CBDO-DGE reaction product or from CHDM in the case of the CHDM/CBDO-DGE reaction product.

High molecular weight, or chain extended, epoxy resins were prepared. High molecular weight CBDO-DGE/CBDO and CBDO-DGE/CHDM products were prepared using the crude commercial CBDO-DGE which contained TBAB. Without wishing to be bound by any particular theory, it is believed that TBAB is able to catalyze the reaction between the CBDO-DGE epoxy groups and the CBDO and CHDM hydroxyl groups. FIG. 7 shows a synthesis of a high molecular weight CBDO-DGE based epoxy resin from the reaction of CBDO or CHDM with CBDO-DGE in the presence of sodium hydroxide and a phase transfer catalyst (TBAB). In the final product, R is derived from CBDO in the case of the CBDO/CBDO-DGE reaction product or from CHDM in the case of the CHDM/CBDO-DGE reaction product.

A mixture of 10 g of crude commercial CBDO-DGE (including the TBAB retained from its synthesis) was mixed with 3.8 g of CBDO. These reagents were combined in a 20 mL glass flask and the mixture vigorously stirred with a Teflon®-coated magnetic stir bar while the glass reaction flask was immersed in a silicone oil bath at 100° C. for 30 minutes. During the reaction, the solution did not change color. The solution was removed from the heat and allowed to cool. Once cooled, the solution was mixed on an IKA VWR Mini Vortexer MV1 for 20 seconds. The solution became warm to the touch, turned yellow and solidified.

In order to purify the product, 2.0 g were placed in 20 mL of distilled water in a 20 mL glass vial with a Teflon®-coated magnetic stir bar and heated to 75° C. At approximately 55° C. the product melted. After 15 minutes, the solution was removed from heat and allowed to cool. The phases separated into a milky-yellow organic phase and a water phase. The water was decanted and the remainder of the water was boiled off at 100° C. with nitrogen as a carrier gas via the technique described previously. The resultant high molecular weight epoxy resin was a clear yellow in color. This material is referred to as CBDO-DGE/CBDO.

Figure 8:
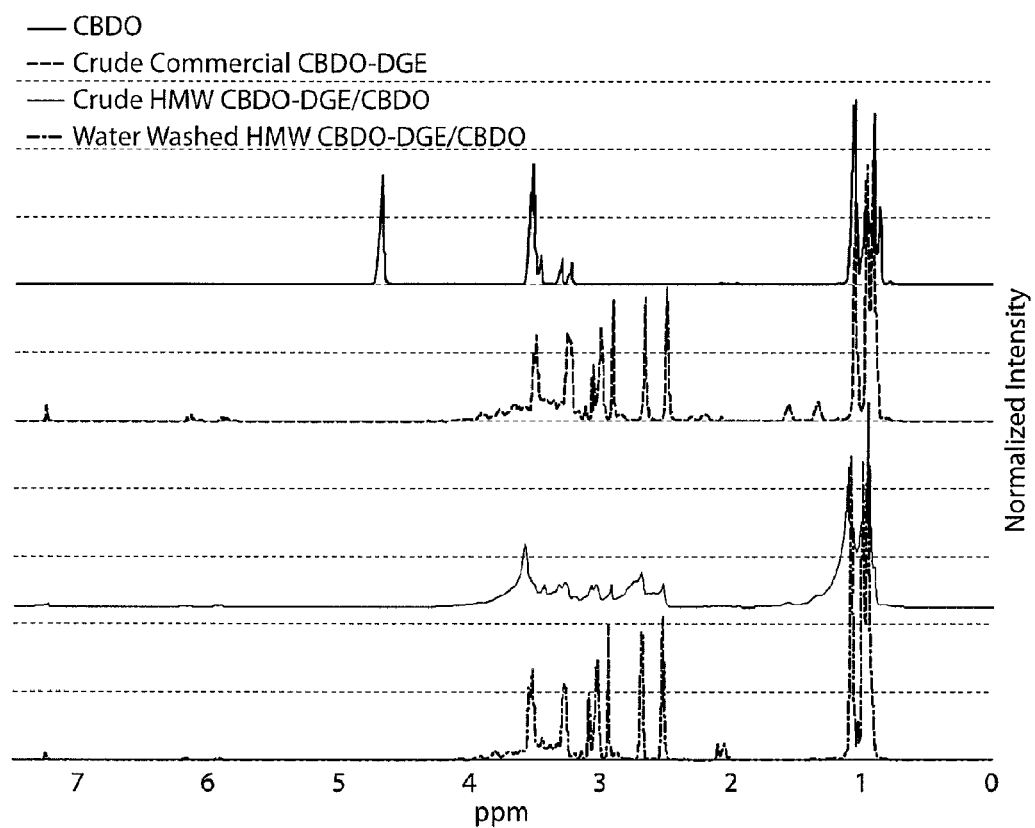
FIG. 8 shows Representative $^1$H-NMR spectra of CBDO, commercial CBDO-DGE, crude CBDO-DGE/CBDO, and water washed CBDO-DGE/CBDO.

FIG. 8 shows Representative $^1$H-NMR spectra of CBDO, commercial CBDO-DGE, crude CBDO-DGE/CBDO, and water washed CBDO-DGE/CBDO. As shown in FIG. 8, it is unclear whether or not all of the CBDO reacted with the crude commercial CBDO-DGE. As both TBAB and CBDO dissolve in water, the CBDO-DGE/CBDO product was purified using the water wash method. FIG. 8 shows the NMR spectrum of the purified CBDO-DGE/CBDO. From the NMR data alone, it is difficult to determine the extent of the reaction because the CBDO peaks overlap with the CBDO-DGE peaks, and both would be expected to overlap with the peaks from the CBDO-DGE/CBDO high molecular weight product. The evidence for the success of this reaction instead comes from the observation that the product solidified at room temperature. A more definitive result comes from an attempt to synthesize a high molecular weight CBDO-DGE/CHDM epoxy, as the CHDM peaks are distinct from those of the CBDO and should remain evident in the water washed product if incorporation was successful.

Figure 9:
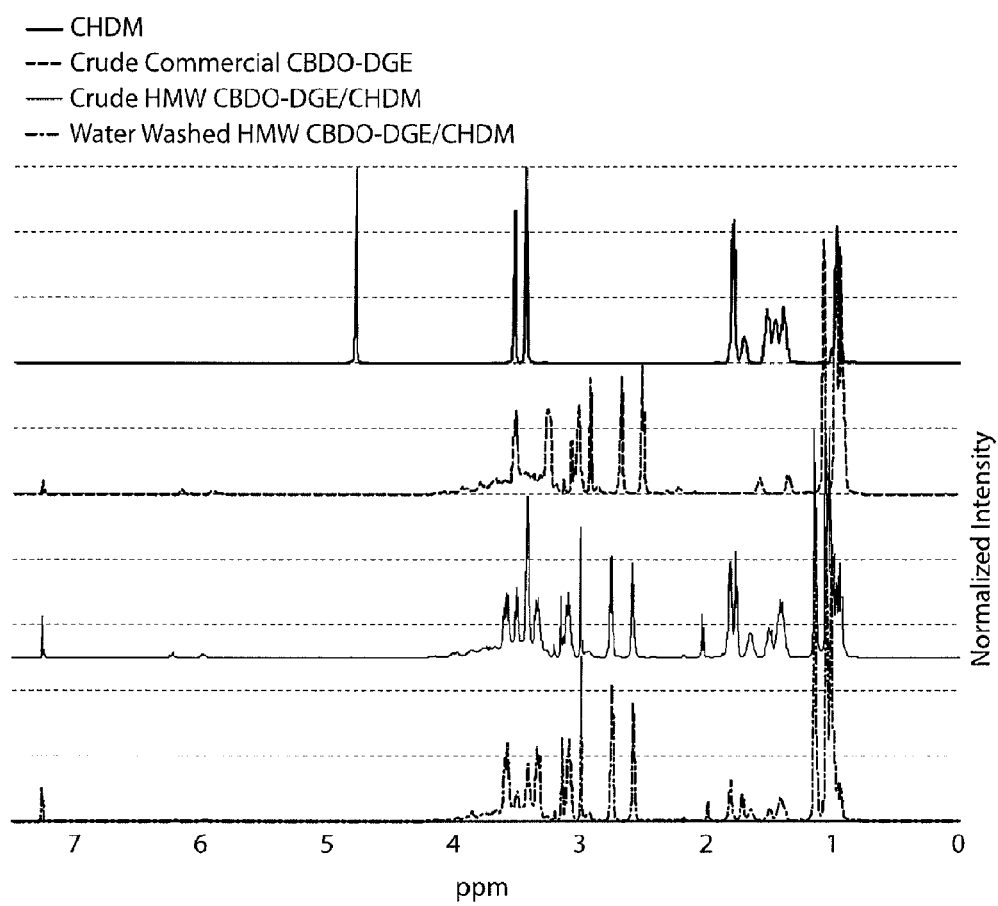
FIG. 9 shows Representative $^1$H-NMR spectra of CHDM, commercial CBDO-DGE, crude CBDO-DGE/CHDM and water washed CBDO-DGE/CHDM.

FIG. 9 shows Representative $^1$H-NMR spectra of CHDM, commercial CBDO-DGE, crude CBDO-DGE/CHDM and water washed CBDO-DGE/CHDM. As seen in FIG. 9, the NMR spectrum does indeed confirm that the CHDM reacted with the CBDO-DGE. This conclusion can be made because the peaks found between 1.5 and 2 ppm are unique to CHDM and represent the ten hydrogens on the cyclohexane ring. Likewise, both TBAB and CHDM dissolve in water, and the CBDO-DGE/CHDM product was purified using the water wash method. Nevertheless, as FIG. 9 shows, the NMR spectrum of the water washed CBDO-DGE/CHDM still contains the aforementioned peaks between 1.5 and 2 ppm that are unique to the CHDM, in addition to showing a higher viscosity at room temperature than the CBDO-DGE. For a one to one molar ratio of CBDO to CHDM in the high molecular weight CBDO-DGE/CHDM product, one would expect a ratio of integrations of the peaks in the 1.5-2 ppm range (10 hydrogens on the cyclohexane ring) to the peaks in the 3.25-3.5 ppm range (2 hydrogens on the cyclobutane ring) to be 10:2. In this case, the ratio was approximately 10:6, implying one CHDM unit for every three CBDO units and supporting the conclusion that high molecular weight materials may be produced in the molecular weight range desirable for can coating epoxies, such as several thousand g/mol or more.

In some embodiments, the molecular weight of the epoxy is sufficiently low that the epoxy remains a liquid at room temperature. For example, the epoxy may contain only one to a few monomer units. In adhesion applications, the molecular weight may be selected to provide a viscosity similar to that of the amine hardener component. In can coating applications, the epoxy may have similar or even larger molecular weights, such as a molecular weight between about 2500 g/mol and about 4000 g/mol.

Example 3

Crosslinking of CBDO-DGE and Comparisons

Figure 10:
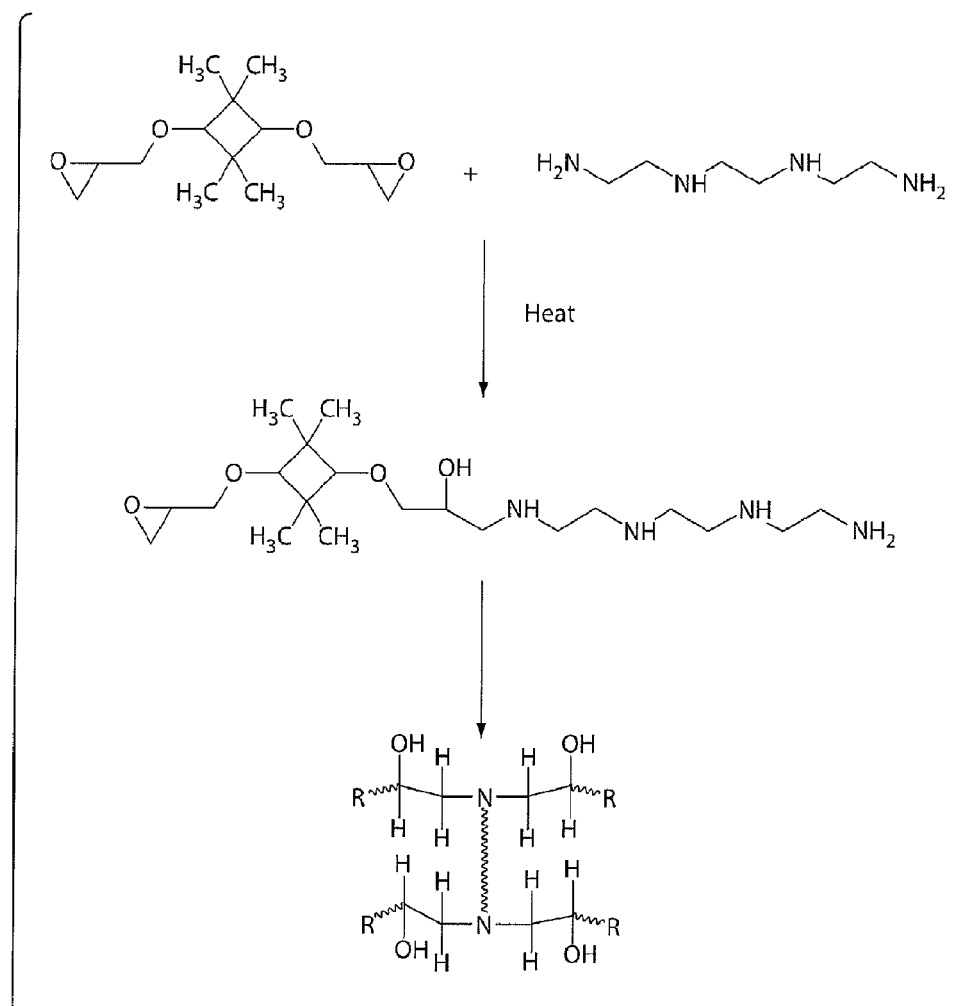
FIG. 10 shows a reaction of 2,2,4,4-tetramethyl-1,3-cyclobutanediol diglycidyl ether (CBDO-DGE) and triethylenetetramine (TETA) to form a crosslinked epoxy network.

CBDO-DGE was crosslinked with TETA in order to form solid networks suitable for further characterization. Based on the epoxy equivalent weight calculated for CBDO-DGE (128.17 g/epoxy equivalent), 1 g of TETA crosslinker is sufficient to crosslink 5.34 g of CBDO-DGE at the desired 1:1 stoichiometry of amine hydrogens to epoxy groups. Therefore, 2.0256 g CBO-DGE and 0.4192 g of TETA were placed in a SpeedMixer (FlackTek, Inc., model DAC 150 FVZ) in order to rapidly and evenly mix the TETA and CBDO-DGE, preferably without introducing air. In some embodiments, the viscosity is sufficiently high that bubbles may get trapped in the mix and create undesirable voids. The total mass of the samples were also approximately 2 g. Following mixing, the samples were cured in an oven at 60° C., 100° C., or 140° C. for 12, 4, or 1 hours respectively, as well as in a stepwise fashion: 60° C. for 30 minutes, then 100° C. for four hours (100° C. stepwise), or 60° C. for two hours, 100° C. for two hours, then 140° C. for one hour (140° C. stepwise). Stepwise curing was found to minimize the cure exotherm and associated thermal degradation while ensuring complete crosslinking. FIG. 10 shows an initial synthesis reaction as well as a reaction of an epoxy resin with TETA in order to form a highly crosslinked network.

To assess the thermal stability and glass transition temperature ($T_g$) of the crosslinked product of the first CBDO-DGE synthesis, TGA and DSC were performed following network formation with TETA at 60° C. for approximately 12 hours. Following ASTM D7426-08, the glass transition temperature ($T_g$) of the TETA crosslinked samples was obtained using a TA Instruments Q200 differential scanning calorimeter. Likewise, thermogravimetric analysis (TGA) was performed using a TA Instruments Q50 thermogravimetric analyzer.

In the case of the crude CBDO-DGE (i.e., with residual TBAB still present), TGA gave a $T_{onset}$ value (temperature at 5% mass loss) of about 232° C. and a $T_{max}$ (temperature at maximum degradation rate) of about 320° C., with no evidence of residual dichloromethane, water or epichlorohydrin observed. From DSC analysis (standard heat/cool/heat type), however, the $T_g$ values obtained were much lower than expected (16° C. during 1st cooling cycle, 20° C. during $2^{nd}$ heating cycle). These results, coupled with the $^1$H-NMR data, imply that residual TBAB negatively impacts the properties of the crosslinked CBDO-DGE.

Comparison of crosslinked networks: As a comparison, crosslinking of BADGE (bisphenol A diglycidyl ether), CHDM-DGE (cyclohexanedimethanol diglycidyl ether) and water washed CBDO-DGE with TETA was attempted under three different conditions (60° C./12 hours, 100° C./4 hours, 140° C./1 hour) in order to ensure that optimally cured materials were produced in all cases. The CBDO-DGE and BADGE were successfully crosslinked at 60° C. and 100° C. while the CHDM-DGE was successfully crosslinked only at 60° C., with obvious thermal degradation occurring at higher crosslinking temperatures.

In general, higher $T_g$, $T_{onset}$ and $T_{max}$ values were observed in samples crosslinked at the highest cure temperature at which degradation did not occur. From the DSC and TGA obtained, it was determined that the washed CBDO-DGE material crosslinked at 100° C. yielded $T_{onset}$ and $T_{max}$ values of 313° C. and 382° C. respectively, vs. 340° C. and 364° C. for the equivalent BADGE network. In contrast, the CHDM-DGE network gave a significantly lower $T_g$ value in spite of the fact that CHDM-DGE is a structural isomer of CBDO-DGE. This result confirms the importance of the rigidity imparted by the CBDO.

It was also found that the CBDO-DGE/TETA crosslinked product using CBDO-DGE washed with acetic acid and cured at 60° C. for 24 hours had a $T_g$ of about 60-86° C., while curing the same cross-linked product at 100° C. for 4 hours provided a $T_g$ of about 68-82° C., vs. 35° C. for the water washed material, approaching that of BADGE (~100-120° C. depending on curing conditions). The desirable softening point for can coatings is typically 80-100° C.

Table 1 lists the DSC and TGA results for TETA-crosslinked samples of BADGE, CHDM-DGE, water washed CBDO-DGE, acid washed CBDO-DGE and water washed commercially made CBDO-DGE.

TABLE 1

Thermal Properties (DSC and TGA results)

| Sample | 60° C., 12 hrs | 60° C., 24 hrs | 100° C., 4 hrs | 60° C., 2 hrs, 100° C., 2 hrs, 140° C. 1 hr |
|---|---|---|---|---|
| BADGE | $T_g$ (1$^{st}$) = 101° C.<br>$T_g$ (2$^{nd}$) = 107° C.<br>$T_{onset}$ = 340° C.<br>$T_{max}$ = 364° C. | | $T_g$ (1$^{st}$) = 116° C.<br>$T_g$ (2$^{nd}$) = 121° C.<br>$T_{onset}$ = 343° C.<br>$T_{max}$ = 362° C. | $T_g$ (1$^{st}$) = 111 ± 3° C. $T_g$ (2$^{nd}$) = 117 ± 2° C.<br>$T_{onset}$ = 369 ± 3° C.<br>$T_{max}$ = 380 ± 2° C. |
| CHDM | $T_g$ (1$^{st}$) = 27° C.<br>$T_g$ (2$^{nd}$) = 34° C.<br>$T_{onset}$ = 290° C.<br>$T_{max}$ = 315° C. | | | |
| CBDO-DGE, Water Washed | $T_g$ (1$^{st}$) = 28° C.<br>$T_g$ (2$^{nd}$) = 35° C.<br>$T_{onset}$ = 247° C.<br>$T_{max}$ = 338° C. | | $T_g$ (1$^{st}$) = 49° C.<br>$T_g$ (2$^{nd}$) = 53° C.<br>$T_{onset}$ = 232° C.<br>$T_{max}$ = 320° C. | |
| CBDO-DGE, Acid Washed | | $T_g$ (1$^{st}$) = 70 ± 13° C.<br>$T_g$ (2$^{nd}$) = 84 ± 4° C.<br>$T_{onset}$ = 326 ± 1° C.<br>$T_{max}$ = 381 ± 1° C. | $T_g$ (1$^{st}$) = 69° C.<br>$T_g$ (2$^{nd}$) = 82° C.<br>$T_{onset}$ = 334° C.<br>$T_{max}$ = 385° C. | |
| Commercial CBDO-DGE, Water Washed | | | | $T_g$ (1$^{st}$) = 65 ± 1° C.<br>$T_g$ (2$^{nd}$) = 74 ± 2° C.<br>$T_{onset}$ = 366 ± 4° C.<br>$T_{max}$ = 370 ± 6° C. |

(1$^{st}$ is 1$^{st}$ Cooling; 2$^{nd}$ is 2$^{nd}$ heating)

From the DSC data, the glass transition temperature of the acid washed product exhibited an average increase of approximately 35° C. over the water washed product. The acid washed CBDO-DGE cured at 100° C. for four hours gave a $T_g$ range (69° C.-82° C.) approaching that of BADGE cured under identical conditions (101° C.-107° C.). In addition, acid washed CBDO-DGE gave networks whose $T_{onset}$ and $T_{max}$ values increased by approximately ~100° C. and ~45° C., respectively, vs. networks based on water-washed CBDO-DGE. These findings confirmed the hypothesis that residual TBAB and residual sodium hydroxide may both reduced the glass transition temperature and thermal stability of networks based on CBDO-DGE. These analyses also confirmed the much lower glass transition temperature and thermal stability of CHDM-DGE based networks prepared in an identical fashion; as CHDM and CBDO are structural isomers, this finding further emphasized the performance characteristics of the CBDO monomer. The CBDO used was a mix of isomers, and the lab made and commercially made CBDO-DGE materials do not have the same cis/trans ratio, a parameter known to affect the performance of materials based on CBDO. It is known that poly(ethylene teterphthalate-co-2,2,4,4-tetramethylcyclobutane terephthalate) copolyesters, when synthesized from a CBDO monomer with a higher cis/trans ratio, displayed higher impact properties. This is believed to be due to the higher degree of coiling and kinking of the material. Thermal testing was not performed but it is feasible to conclude that since differences in the cis/trans ratio affected the impact properties, that the thermal and mechanical properties could be sensitive to this ratio as well. The average glass transition temperature of the stepwise cured water washed commercial CBDO-DGE was approximately 10° C. lower than the acid washed lab made material and approximately 40° C. lower than the BADGE material cured at the same stepwise process. One possible explanation for this may be the occurrence of side reactions as a consequence of reduced thermal and compositional homogeneity in a larger reaction volume, which might have resulted in a higher epoxy equivalent weight than was assumed.

In addition, mechanical and physical properties were also compared as determined using dynamic mechanical analysis (DMA), Shore D hardness testing, and density testing.

Figure 11:
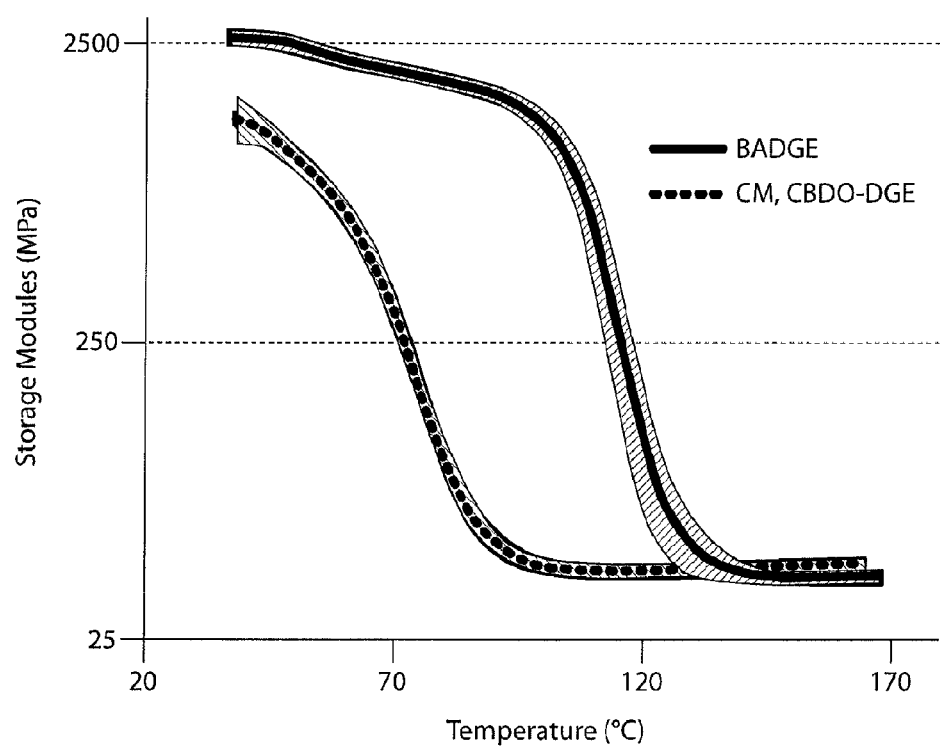
FIG. 11 shows a plot of average DMA storage modulus curves for TETA-crosslinked bisphenol A diglycidyl ether (BADGE) and water washed commercial CBDO-DGE.
Figure 12:
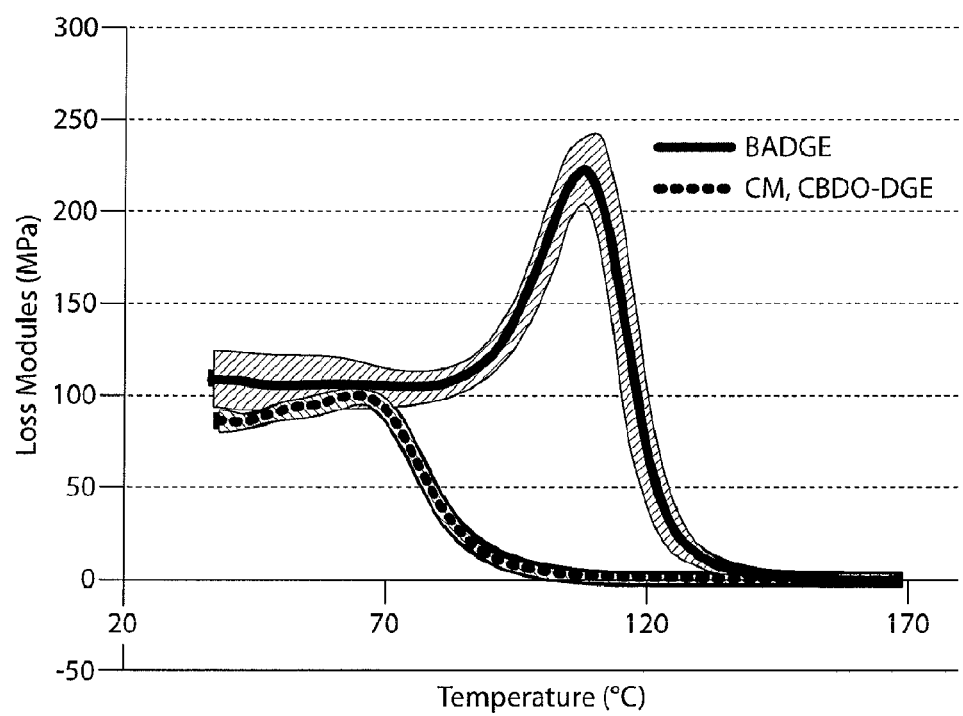
FIG. 12 shows a plot of average DMA loss modulus curves for TETA-crosslinked BADGE and water washed commercial CBDO-DGE.

Dynamic Mechanical Analysis: Initial DMA analyses of TETA-crosslinked BADGE samples gave evidence (via the observation of an increase in storage modulus at temperatures above 100° C.) of further curing of the sample in the instrument and during the test. Specimens made for DMA analysis were then stepwise cured and the last step involved curing for one hour at 140° C. This eliminated any further curing in the instrument and, therefore, an increase in storage modulus was no longer observed in the data. FIGS. 11 and 12 show average storage and loss modulus curves, respectively, for TETA-crosslinked networks based on BADGE (n=5) and water washed commercial CBDO-DGE (n=6), with the shaded zones around the curves indicative of one standard deviation. From these plots the BADGE-based networks material gave a higher stiffness and alpha transition temperature. The average storage modulus value for BADGE network at 40° C. was approximately 2600 MPa. The value for the water washed commercial CBDO-DGE network was 1300 MPa. Likewise, from the loss modulus plot (FIG. 12), the $T_\alpha$ value for the BADGE network was approximately 110° C. The $T_\alpha$ value for the water washed commercial CBDO-DGE network was approximately 66° C. As shown in FIG. 12, the BADGE network exhibited a sharp alpha transition. The water washed commercial CBDO-DGE gave a broader, weaker alpha transition. This may be due to the presence of residual impurities within the CBDO-DGE material (i.e. monoglydicyl ethers, CBDO-DGE/epichlorohydrin reaction products, and compounds where ring-closing to form the final epoxy groups was incomplete), coupled with the shift in the optimal epoxy/amine ratio these impurities would cause. Some part of this effect may also be due to the presence of a mixture of cis and trans isomers of CBDO in the final network.

An empirical model validated with highly crosslinked epoxies was used to calculate the average crosslink densities in these systems based on the modulus in the rubbery plateau. First, (tensile) storage moduli values taken approximately 50° C. above the alpha transition were converted to shear moduli via the equation 1, where G is shear modulus, E is the elastic (tensile) modulus taken from FIG. 11, and v is Poisson's ratio, which may be assumed to be 0.5 for networks well above their alpha transition. When Poisson's ratio is ~0.5, the expression shown in FIG. 3 simplifies to G=E /3.

$$G = \left[\frac{E}{2(1=v)}\right] \quad (1)$$

Equation 2 provides the relevant relationship between G, the shear modulus (in dynes/cm$^2$; note that 1 MPa=1×10$^7$ dynes/cm$^2$), p, the material density (in g/cm$^3$), and M$_c$, the molecular weight between crosslinks (in g/mol).

$$\text{Log }(G) = \left[\frac{293(p)}{M_c}\right] + 7 \quad (2)$$

The elastic (tensile) modulus (E) value for the TETA-crosslinked BADGE network was taken at about 160° C. to be about 40.5 MPa. Using the average experimental density value for the stepwise cured TETA-crosslinked BADGE network (p=1.1852 g/cm$^3$), a M$_c$ of about 307 g/mol was calculated. Along the same lines, the elastic (tensile) modulus (E) value for the TETA-crosslinked water washed commercial CBDO-DGE network was taken at about 130° C. to be about 43.1 MPa. Using the average experimental density value for the stepwise cured TETA-crosslinked water washed commercial CBDO-DGE (p=1.1279 g/cm$^3$), in contrast, a M$_c$ value of about 286 g/mol was calculated.

These results indicate that the TETA-crosslinked BADGE network appears to have been very effectively crosslinked, given that the M$_c$ measured is actually below the molecular weight of the BADGE itself (about 340 g/mol). This is possible given the higher functionality (f=6) and lower molecular weight (about 146 g/mol) of the TETA coupled with the fact that M$_c$ values reflect the average molar mass of whatever material exists between junction points in a network. The data from the TETA-crosslinked commercial water washed CBDO-DGE network implies slightly less efficient crosslinking, as the M$_c$ in this case was found to be above the molecular weight of CBDO-DGE (about 256 g/mol). This indicates the presence of some unreacted CBDO-DGE and/or impurities in the network.

Based on this analysis, it is clear that the stiffness and alpha transition temperature of the CBDO-DGE based networks could be improved via further increases in sample purity as well as efforts to optimize the reaction stoichiometry during crosslinking. The proximity of the results, however, indicates that the mechanical properties of the networks of the present disclosure approach that of BADGE networks.

Shore D Durometer Hardness: In order to determine the hardness (Shore D Hardness) of the TETA-crosslinked BADGE and CBDO-DGE samples, a Shore D instrument was used following ASTM D2240 in order to obtain the instantaneous hardness of each material. The specimens used for this test were cut from larger samples ranging from 2-5 g in size and cured at multiple curing conditions. Hardness readings were obtained on the upper and lower surfaces of samples. Measurements were taken on stacked specimens with a minimum thickness of approximately 1 centimeter in order to avoid artifacts associated with the hardness of the underlying substrate.

The hardness of the selected materials is listed in Table 2. While TETA-crosslinked acid washed CBDO-DGE, water washed commercial CBDO-DGE and BADGE networks showed similar hardness values, the slightly higher value of the BADGE material was consistent with the higher glass transition temperature of the BADGE-based network. The water washed commercial CBDO-DGE network, when cured in a stepwise fashion, had a higher hardness than the BADGE and CBDO-DGE specimens when cured at a single temperature, likely due to incomplete curing in the latter cases, though this emphasizes how close the hardness values were in these systems. The water washed commercial CBDO-DGE presented a relatively similar hardness as the equivalent BADGE network cured under identical conditions.

TABLE 2

Average Shore D Durometer Hardness Results vs. Composition and Curing Conditions

| Sample (Curing conditions) | Shore D Hardness (Average ± S.D.) |
|---|---|
| Acid Washed CBDO-DGE (60° C., 24 hrs) | 81 ± 3 |
| CHDM-DGE (60° C., 24 hrs) | 77 ± 4 |
| BADGE (60° C., 24 hrs) | 81 ± 3 |
| Acid Washed CBDO-DGE (100° C., 4 hrs) | 78 ± 3 |
| BADGE (100° C., 4 hrs) | 81 ± 1 |
| Waster Washed Commercial CBDO-DGE (60° C., 2 hrs, 100° C., 2 hrs, 140° C., 1 hr) | 84 ± 1 |
| BADGE (60° C., 2 hrs, 100° C., 2 hrs, 140° C., 1 hr) | 88 ± 1 |

The data in Table 2 show that the BADGE material had an average hardness which was just slightly higher than the CBDO-DGE material. This can be attributed to the BADGE molecule with its aromatic rings being slightly more rigid than the four sided ring of CBDO-DGE. Also, hardness reflects crosslink density where the stepwise cure to 140° C. for BADGE and CBDO-DGE provided the highest hardness values for each material. The higher cure temperature allowed for a higher degree of crosslinking.

Density: Density testing was performed following ASTM D792 on TETA-crosslinked BADGE and various TETA-crosslinked CBDO-DGE resins. Data were collected using a Denver TB-124 analytical balance. The samples used for this test were cut from larger samples ranging from 2-5 g in size and cured at multiple curing conditions. The apparent masses of these specimens were measured while immersed in water, allowing the calculation of the specific gravity of the materials; the density of water was then assumed to be 1 g/cm$^3$ for the purposes of calculating density.

Table 3 lists the average densities of the materials tested. Consistent with the presence of aromatic rings, which tend to contribute to higher densities, the BADGE-based material had a slightly higher density value than the CBDO-DGE based material.

TABLE 3

Average Density Measurements

| Sample (Curing conditions) | Density (g/mL) (Average ± S.D.) |
|---|---|
| Acid Washed CBDO-DGE (60° C., 24 hr) | 1.1156 ± 0.0051 |

TABLE 3-continued

Average Density Measurements

| Sample (Curing conditions) | Density (g/mL) (Average ± S.D.) |
|---|---|
| Acid Washed CBDO-DGE (100° C., 4 hr) | 1.1110 ± 0.0025 |
| Water Washed Commercial CBDO-DGE (60° C., 2 hr, 100° C., 2 hr, 140° C., 1 hr) | 1.1279 ± 0.0127 |
| BADGE (60° C., 24 hr) | 1.1795 |
| BADGE (100° C., 4 hr) | 1.1891 |
| BADGE (60° C., 2 hr, 100° C., 2 hr, 140° C., 1 hr) | 1.1852 ± 0.0017 |
| CHDM-DGE (60° C., 24 hr) | 1.1538 |

Table 3 shows that the BADGE material had an average density which was slightly higher than the CBDO-DGE material. This can be attributed to the aromatic rings of the BADGE molecule. These aromatic rings are denser then the four sided ring of CBDO-DGE. This results in BADGE being approximately 10% more dense than the CBDO-DGE material.

Example 4

Adhesive Application

The adhesive properties of the epoxy resin of the present disclosure, e.g. CBDO-DGE, were tested against the equivalent BPA-based diglycidyl ether, BADGE and Loctite® Epoxy Heavy Duty professional epoxy. Both the epoxy resin of the present disclosure and the BPA-based diglycidyl ether were cured with triethylenetetraamine.

Sample Preparation for Single Joint Lap-Shear Test: Test specimens were prepared according to ASTMD 1002-10. Low carbon 1008/1010 steel rectangular test specimens were used. The surface of the specimens was prepared according to ASTM D2651-01. The test specimens were first cleaned with acetone to remove all surface impurities. The surface was then roughened using sand paper (Norton 80-J Grit) followed by dry air blasting to remove all the traces of abrasive and residual impurities. Each reaction mixture was applied immediately on surface and overlap joint was cured at room temperature under constant loading until complete cure. Both samples, BADGE and CBDO-DGE, with TETA crosslinker cured completely in 3 days and were subjected to testing after 5 days (total of 8 days after application). Whereas the commercial epoxy (Loctite®), as the name indicates, cured in 5 minute and samples were subjected to testing 2 days after application.

Testing: Testing was conducted in accordance with ASTMD 1002-10. A universal testing machine Instron-4481 was used with a load frame of 5 KN under tension at crosshead speed of 0.05 inch/min (1.27 mm/min) Test specimens were placed in the grips of the testing machine such that outer 25 mm of each end are in contact with the jaws and so that the long axis of the test specimen coincides with the direction of the applied pull through the center line of the grip assembly. A total of 5 samples for each formulation were tested at room temperature. Data obtained was recorded using Blue Hill software (2.6 versions). The data is summarized in Table 4.

TABLE 4

Adhesive Data

| Sample # | Area (cm$^2$) | Area [mm$^2$] | Joint Width (mm) | Joint Length (mm) | Stress at break (calculated) [Mpa] | Load at Machine Break (N) |
|---|---|---|---|---|---|---|
| Sample: Steel samples subjected to test after 8 days of adhesive application Load = 5 KN; Rate = 0.05 in/min; TYPE: Tension CBDO__DGE/TETA(RT Cure) | | | | | | |
| 1 | 3.86 | 386.36 | 25.17 | 15.35 | 6.73 | 2599 |
| 2 | 4.02 | 401.96 | 25.17 | 15.97 | 8.76 | 3523 |
| 3 | 4.10 | 409.70 | 25.29 | 16.20 | 11.68 | 4784 |
| 4 | 4.13 | 413.38 | 25.16 | 16.43 | 8.54 | 3530 |
| 5 | 4.17 | 417.23 | 25.41 | 16.42 | 10.88 | 4540 |
| | | | | Average | 9.32 | MPa |
| | | | | SD | 1.98 | MPa |
| Sample: Steel samples subjected to test after 8 days of adhesive application Load = 5 KN; Rate = 0.05 in/min; TYPE: Tension DGBA/TETA(RT Cure) | | | | | | |
| 1 | 3.68 | 367.75 | 25 | 14.71 | 6.39 | 2349 |
| 2 | 3.75 | 375.25 | 25 | 15.01 | 8.18 | 3068 |
| 3 | 3.93 | 392.50 | 25 | 15.7 | 7.64 | 3000 |
| 4 | 3.73 | 373.00 | 25 | 14.92 | 6.87 | 2564 |
| 5 | 3.70 | 369.50 | 25 | 14.78 | 6.46 | 2388 |
| | | | | Average | 7.11 | MPa |
| | | | | SD | 0.78 | MPa |
| Sample: Steel samples subjected to test after 2 days of adhesive application Load = 5 KN; Rate = 0.05 in/min; TYPE: Tension Commerical Epoxy (Loctite, 5 min) | | | | | | |
| 1 | 3.58 | 358.00 | 24.47 | 14.63 | 7.01 | 2511 |
| 2 | 3.38 | 337.82 | 24.84 | 13.60 | 9.97 | 3369 |
| 3 | 3.13 | 313.35 | 24.79 | 12.64 | 12.89 | 4039 |
| 4 | 3.14 | 313.72 | 24.80 | 12.65 | 7.78 | 2440 |
| 5 | 3.22 | 321.69 | 24.26 | 13.26 | 12.66 | 4071 |
| | | | | Average | 10.06 | MPa |
| | | | | SD | 2.70 | MPa |

The adhesive comprising the epoxy resin of the present disclosure exhibited superior adhesion compared to the BPA-based diglycidyl ether equivalent, 9.32 average MPa vs. 7.11 average MPa, and adhesive levels more or less equivalent to that of the commercial epoxy resin.

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

What is claimed is:

1. An adhesive composition comprising an epoxy resin represented by:

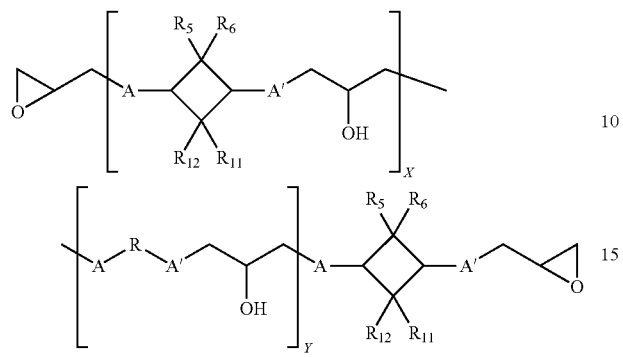

wherein A and A' are each independently selected from the group consisting of O or S;

wherein $R_5$, $R_6$, $R_{11}$, and $R_{12}$ are each independently selected from hydrogen or a $C_1$ - $C_6$ straight chain or branched alkyl or alkenyl group, wherein the alkyl or alkenyl group is optionally substituted with one or more substituents, each of which is independently selected from $NH_2$, OH, $CF_3$, CN, $CO_2H$, C(O)H or halogen, provided that at least one of $R_5$, $R_6$, $R_{11}$, and $R_{12}$ is not hydrogen; wherein adjacent R groups may optionally form a fused ring selected from a $C_5$ - $C_7$ membered aromatic ring, or a $C_3$ - $C_8$ cycloalkyl or heterocycle;

wherein R is derived from an aliphatic or cycloaliphatic molecule comprising at least two functional groups;

X is 1 or greater;

Y is 0 or greater; and wherein the epoxy resin has a weight average molecular weight of less than about 2,000 Daltons and wherein the epoxy resin has a reduced potential to release endocrine disrupting compounds compared to bisphenol A and related phenolic compounds.

2. The adhesive composition of claim 1, wherein R is derived from a diglycidyl ether of a diol selected from the group consisting of:

2,2,4,4-tetramethyl-1,3-cyclobutanediol;
3,3,4,4,5,5-hexamethyl-1,2-cyclopentanediol;
2,2,4,4,5,5-hexamethyl-1,3-cyclopentanediol;
3,3,4,4,5,5,6,6-octamethyl-1,2-cyclohexanediol;
2,2,4,4,5,5,6,6-octamethyl-1,3-cyclohexanediol;
2,2,3,3,5,5,6,6-octamethyl-1,4-cyclohexanediol;
3,3,4,4,5,5,6,6,7,7-decamethyl-1,2-cycloheptanediol;
2,2,4,4,5,5,6,6,7,7-decamethyl-1,3-cycloheptanediol;
2,2,3,3,5,5,6,6,7,7-decamethyl-1,4-cycloheptanediol;
3,3,4,4,5,5,6,6,7,7,8,8-dodecamethyl-1,2-cyclooctanediol;
2,2,4,4,5,5,6,6,7,7,8,8-dodecamethyl-1,3-cyclooctanediol;
2,2,3,3,5,5,6,6,7,7,8,8-dodecamethyl-1,4-cyclooctanediol;
2,2,3,3,4,4,6,6,7,7,8,8-dodecamethyl-1,5-cyclooctanediol;
4,4-dimethyl-1-cyclobutanone-2,3-diol;
1,2-cyclobutanedione-3,4-diol;
4,4-dimethyl-2-cyclobutanone-1,3-diol;
1,3-cyclobutanedione-2,4-diol;
cyclohexanedimethanol; and
diol derivatives of norbornane, norbornene, bicycle[2.2.2]octane, cubane and adamantine.

3. An adhesive composition comprising an epoxy resin represented by:

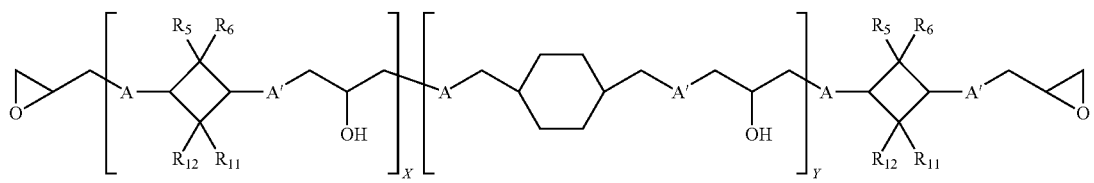

wherein A and A' are each independently selected from the group consisting of O or S;

wherein $R_5$, $R_6$, $R_{11}$, and $R_{12}$ are each independently selected from hydrogen or a $C_1$ - $C_6$ straight chain or branched alkyl or alkenyl group, wherein the alkyl or alkenyl group is optionally substituted with one or more substituents, each of which is independently selected from $NH_2$, OH, $CF_3$, CN, $CO_2H$, C(O)H or halogen, provided that at least one of $R_5$, $R_6$, $R_{11}$, and $R_{12}$ is not hydrogen;

X is 1 or greater;

Y is 1 or greater; and wherein the epoxy resin has a weight average molecular weight of less than about 2,000 Daltons and wherein the epoxy resin has a reduced potential to release endocrine disrupting compounds compared to bisphenol A and related phenolic compounds.

4. The adhesive composition of claim 1, wherein A and A' are both O; and $R_5$, $R_6$, $R_{11}$, and $R_{12}$ are each independently selected from hydrogen or a $C_1$ - $C_6$ straight chain or branched alkyl groups.

5. The adhesive composition of claim 4, wherein $R_5$, $R_6$, $R_{11}$, and $R_{12}$ are each independently selected from methyl or ethyl groups.

6. The adhesive composition of claim 1, wherein A and A' are both O; and $R_5$, $R_6$, $R_{11}$, and $R_{12}$ are each a methyl group.

7. The adhesive composition of claim 1, wherein the epoxy resin has a viscosity of less than about 100 poise at 25° C. measured as a 40% weight solution of resin solids in methyl ethyl ketone or equivalent solvent.

8. The adhesive composition of claim 1, wherein the epoxy resin has the following structure:

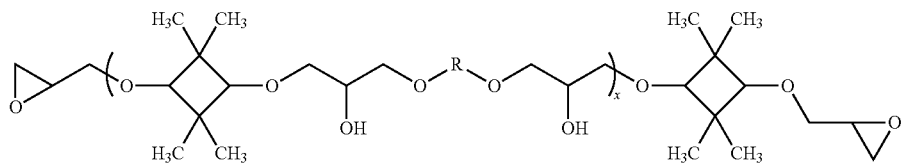
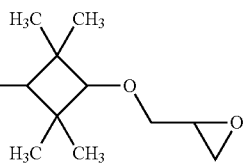

and wherein R is derived from

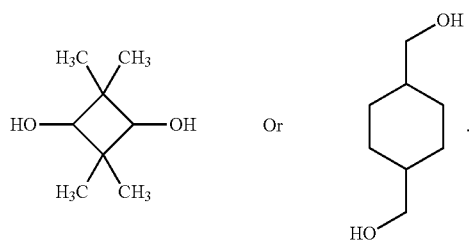

9. The adhesive composition of claim 1, wherein the epoxy resin is represented by:

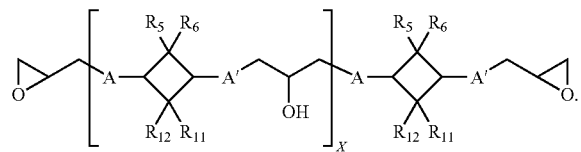

10. A cured adhesive composition comprising the reaction product of epoxy resin of claim 1 and a curative compound, wherein the cured epoxy resin has a reduced potential to release endocrine disrupting compounds compared to cured epoxy resins comprising bisphenol A and related phenolic compounds.

11. The adhesive composition of claim 10, wherein the curative compound is a formaldehyde hardener, a polyamine hardener or a polythiol hardener.

12. The adhesive composition of claim 1, wherein the epoxy resin is a chain extended epoxy resin prepared by:
  a. reacting a first substituted 1,3-cyclobutanediol molecule with epichlorohydrin in the presence of a first catalyst to form a diglycidyl ether, and
  b. reacting the diglycidyl ether with a second substituted 1,3-cyclobutanediol molecule in the presence of a second catalyst to form the chain extended epoxy resin.

13. The adhesive composition of claim 12, wherein the first substituted 1,3-cyclobutanediol diglycidyl ether is 2,2,4,4-tetramethyl-1,3-cyclobutanediol diglycidyl ether, the second substituted 1,3-cyclobutanediol molecule is 2,2,4,4-tetramethyl-1,3-cyclobutanediol, and the catalyst is tetrabutyl ammonium hydrogen bisulfate.

* * * * *

UNITED STATES PATENT AND TRADEMARK OFFICE
CERTIFICATE OF CORRECTION

PATENT NO. : 9,434,867 B2  
APPLICATION NO. : 14/860131  
DATED : September 6, 2016  
INVENTOR(S) : Daniel Schmidt Page 1 of 1

It is certified that error appears in the above-identified patent and that said Letters Patent is hereby corrected as shown below:

In the Claims

In Claim 1:

At Column 27, Line 22, delete "0" and replace it with "O".

In Claim 8:

At Column 29, Line 18, within the structure, delete "Or" and replace it with "or".

In Claim 13:

At Column 30, Line 29, delete "diglycidyl ether" and replace it with "molecule".

Signed and Sealed this  
Tenth Day of January, 2017

Michelle K. Lee  
*Director of the United States Patent and Trademark Office*